(12) United States Patent
Takahashi et al.

(10) Patent No.: US 8,303,910 B2
(45) Date of Patent: Nov. 6, 2012

(54) BIOSENSOR

(75) Inventors: Mie Takahashi, Ehime (JP); Ryoko Kawamata, Ehime (JP)

(73) Assignee: Panasonic Corporation, Osaka (JP)

( * ) Notice: Subject to any disclaimer, the term of this patent is extended or adjusted under 35 U.S.C. 154(b) by 29 days.

(21) Appl. No.: 12/990,313

(22) PCT Filed: Apr. 23, 2009

(86) PCT No.: PCT/JP2009/001860
§ 371 (c)(1),
(2), (4) Date: Oct. 29, 2010

(87) PCT Pub. No.: WO2009/136477
PCT Pub. Date: Nov. 12, 2009

(65) Prior Publication Data
US 2011/0045579 A1  Feb. 24, 2011

(30) Foreign Application Priority Data

May 7, 2008  (JP) ................................ 2008-120853
Jul. 16, 2008  (JP) ................................ 2008-184354
Jul. 31, 2008  (JP) ................................ 2008-197122

(51) Int. Cl.
*G01N 15/06* (2006.01)
*G01N 33/00* (2006.01)
*G01N 33/48* (2006.01)

(52) U.S. Cl. ......... 422/503; 422/50; 422/68.1; 422/502; 422/504; 422/507

(58) Field of Classification Search .................... 422/50, 422/68.1, 502, 503, 504, 507
See application file for complete search history.

(56) References Cited

U.S. PATENT DOCUMENTS

| 4,861,711 A | 8/1989 | Friesen et al. |
| 7,575,915 B2 | 8/2009 | Nadaoka et al. |
| 2003/0190690 A1 | 10/2003 | Takahashi et al. |
| 2005/0227371 A1 * | 10/2005 | Gokhan ........................ 436/514 |

FOREIGN PATENT DOCUMENTS

| EP | 0284232 | 10/2002 |
| EP | 1353181 | 10/2003 |
| JP | 07-078503 | 8/1995 |
| JP | 2504923 | 4/1996 |
| JP | 2890384 | 2/1999 |
| JP | 3553045 | 5/2004 |
| JP | 2005-257468 | 9/2005 |
| JP | 2007-530946 | 11/2007 |
| WO | 03/014741 | 2/2003 |
| WO | 2005/095967 | 10/2005 |

* cited by examiner

*Primary Examiner* — Brian J Sines
(74) *Attorney, Agent, or Firm* — Hamre, Schumann, Mueller & Larson, P.C.

(57) ABSTRACT

Provided is a biosensor with precision, high accuracy, and high sensitivity capable of increasing measurement accuracy while allowing measurements to be performed anywhere at any time by anyone, and allowing measurement with a small amount of specimen. In a biosensor including a specimen application portion (12) and a development flow channel (2), the specimen application portion (12) is configured such that an application space (9) is enclosed by a space-forming member (8) made of a liquid impermeable material, and a reaction reagent (14) that contains a labeling-reagent is retained in a position facing the application space (9) of the space-forming member (8) in the specimen application portion (12) so that the reaction reagent can be dissolved into a liquid specimen applied to the application space (9). Thus, it is possible to reduce the amount of specimen required for measurement, also completely dissolve the labeling-reagent and cause the labeling-reagent to react and develop with the entire liquid specimen, allowing measurement with high accuracy and high sensitivity.

23 Claims, 17 Drawing Sheets

STEP1

STEP2

STEP3

STEP4

STEP5

STEP6

BIOSENSOR

TECHNICAL FIELD

The present invention relates to a biosensor as a sheet-like analyzing device that analyzes an analyte in a liquid specimen using an immunological measurement method.

BACKGROUND ART

In recent years, home care and community health care in doctor's offices and clinics have improved and the number of early diagnoses and the number of urgent laboratory tests have increased. Against this backdrop, analyzing devices have been demanded that allow quick and easy measurement with high accuracy even if users are not medical technologists. Thus, small analyzing devices for POCT (Point of Care Testing) that can perform precision measurements in a short time without complicated operations have received attention.

Generally, POCT is a generic name for inspections conducted in positions "close to patients", for example, in consulting rooms of practitioners and specialists, hospitals, and clinics for outpatients. POCT has been a notable method that is quite useful for improving the quality of diagnoses such that a doctor quickly judges an inspection result, immediately performs treatment, and monitors the process of the treatment and the prognosis. Inspections conducted by such small analyzing devices can reduce the cost of transporting specimens, the cost of equipment, and the cost of unnecessary inspections, thereby reducing the total inspection cost as compared with inspections conducted in central inspecting rooms. In the U.S. where rational hospital management is advancing, the POCT market has rapidly expanded and is expected to grow worldwide, including Japan.

In a dry-type biosensor as analysis element typified by an immuno-chromatographic sensor, an adjustment of a reagent is not necessary and an analyte contained in a liquid specimen such as blood and urine to be measured can be analyzed by a simple operation such as dropping the liquid specimen on the biosensor. Currently, a large number of dry-type biosensors have been put into practical use as representative POCT because dry-type biosensors are quite useful for easily and quickly analyzing an analyte in a liquid specimen.

In an immuno-chromatographic sensor (hereinafter abbreviated as a chromatographic sensor) using an antigen-antibody reaction, a sensing reaction is performed with high specificity and a strong binding force. Thus, the chromatographic sensor provides more excellent characteristics than other sensors in an analysis of a physiologically active substance with an extremely low concentration. Currently, using this principle, many diagnostic agents such as pregnancy diagnostic agents, cancer marker diagnostic agents, or cardiac muscle marker diagnostic agents have been commercially available.

As a configuration of a chromatographic sensor, Patent Document 1 discloses an assay device that causes a substance to flow in a plurality of sections (regions) that can communicate with each other by a capillary flow on same plane, that is, on one flat solid support, and determines whether an analyte is present or not in a liquid specimen.

Patent Documents 2 and 3 disclose an analyzing device that detects or measures one of a pair of combined components having immunological binding properties in a liquid.

The above-described methods in Patent Documents 1 to 3 are all described for a configuration of an immunological assay device having a specific reaction, and the device is made of a material such that a liquid specimen can be developed by a capillary force (force caused by capillarity). For example, Patent Document 1 features a configuration such that the flat solid support has a region (first section) in which a tracer that specifically reacts with an analyte is retained, and a region (second section) in which a binder specifically bound to the analyte or the tracer, and the regions (the first section and the second section) are located on the solid support on the same plane and can communicate with each other by a capillary flow. Patent Documents 2 and 3 features a configuration including a sheet-like zone formed of one or more thin pieces placed on the front and rear in a development direction of a liquid specimen and in a contact state where the liquid specimen can be absorbed by each other through edges of the pieces, and a solid support.

An example of a general configuration of a chromatographic sensor typified by Patent Documents 1 to 3 are shown in FIGS. 14A to 14C, 15A, and 15B. A general configuration of the chromatographic sensor includes, on a substrate 1 of a PET sheet or the like, a development flow channel 2, a labeling-reagent retaining portion 4, a specimen application region 5, and a water absorbing portion 6. The development flow channel 2 is formed of a porous carrier such as cellulose nitrate or glass fiber filter paper and partly has a reagent-immobilized portion 3 in which a reagent that specifically reacts with an analyte or a tracer is immobilized. In the labeling-reagent retaining portion 4, a labeling-reagent obtained by labeling a reagent that specifically reacts with an analyte and an immobilized-reagent is retained by a liquid permeable material so that the labeling-reagent is easily dissolved by permeation of the liquid specimen. The specimen application region 5 is provided on the labeling-reagent retaining portion 4 or upstream in a chromatography development direction of the labeling-reagent retaining portion 4, and a liquid specimen is applied on there. The water absorbing portion 6 absorbs water from a developed liquid specimen in a downstream region in the chromatography development direction. On the substrate 1, in order from an upstream side in the chromatography development direction, an upstream end of the labeling-reagent retaining portion 4 is in contact with a downstream end of the specimen application region 5, an upstream end of the development flow channel 2 is in contact with a downstream end of the labeling-reagent retaining portion 4, and an upstream end of the water absorbing portion 6 is in contact with a downstream end of the development flow channel 2. Sensor components other than the substrate 1 (the specimen application region 5, the labeling-reagent retaining portion 4, the development flow channel 2, and the water absorbing portion 6) are all made of a liquid permeable material. In many cases, as shown in FIGS. 15A and 15B, the chromatographic sensor is housed in a hollow casing 51 made of a liquid impermeable material and including a specimen application portion 50 and a result check window 52 so that the reagent-immobilized portion 3 and the specimen application region 5 are partly exposed to the outside.

The development (flow) of the liquid specimen or the like and the measurement principle of the chromatographic sensor will be described. First, the liquid specimen is applied to the specimen application portion 50 in the hollow casing 51. The applied liquid specimen is developed through the specimen application portion 50 while water in the liquid specimen is absorbed by capillarity caused by each construction material for the chromatographic sensor. The liquid specimen developed from the specimen application region 5 and having reached the labeling-reagent retaining portion 4 is further developed downstream while dissolving the labeling-reagent and passes through the reagent-immobilized portion 3 when being developed in the development flow channel 2. The liquid specimen is further developed downstream and water in the liquid specimen is absorbed by the water absorbing portion 6. In case that the liquid specimen contains the analyte, when the analyte reaches the labeling-reagent retaining portion 4, firstly, the analyte undergoes a specific binding reaction with the labeling-reagent to form a "labeling-reagent-analyte complex". The "labeling-reagent-analyte complex" is developed to the development flow channel 2 together with the liquid specimen, and further reaches the reagent-immobilized portion 3. In the reagent-immobilized portion 3, the "labeling-reagent-analyte complex" also undergoes a specific binding reaction with the immobilized-reagent to form a "labeling-reagent-analyte-immobilized-reagent complex". Then, in the reagent-immobilized portion 3, a color reaction caused by the labeling-reagent depending on the concentration of the analyte can be checked through the result check window 52. The general chromatographic sensor typified by this configuration is widely distributed for use in hospitals or home in the market. Herein, a sandwich reaction that forms the "labeling-reagent-analyte-immobilized-reagent complex" is taken as an example of an immune reaction for describing the measurement principle, but a competitive reaction is often used.

In the configuration of the chromatographic sensor, in order to help development of the liquid specimen and retaining the developed liquid specimen, the water absorbing portion 6 made of a material that satisfactorily absorbs liquids is provided adjacent to the development flow channel 2. Also, it is important that when the liquid specimen is applied, the labeling-reagent is discharged from the labeling-reagent retaining portion 4 as quickly and completely as possible, and developed with the development of the liquid. Thus, it has been proved that a porous material or a fiber material is suitable as a construction material for the labeling-reagent retaining portion 4. As a specific example, the labeling-reagent retaining portion 4 is often made of paper, fleece, a porous plastic layer, or a membrane. However, since the labeling-reagent retained by the construction material is permeated to a deep part of the material, a sufficient amount of liquid specimen is often difficult to dissolve. Also, since the construction material and the labeling-reagent are nonspecifically adsorbed during a dry state, the retained labeling-reagent cannot be completely dissolved, and the degree of dissolution of the labeling-reagent differs depending on chromatographic sensors. Thus, when quantitative measurement using the immuno-chromatographic sensor is performed, unfortunately, sufficient accuracy cannot be obtained and measurement with high sensitivity cannot be performed.

Next, it is described with reference to FIGS. 16A to 16F (in FIGS. 16B to 16F, only the chromatographic sensor is shown and the hollow casing 51 is omitted) that a state where the liquid specimen is developed on a conventional general chromatographic sensor shown in FIGS. 15A and 15B when the liquid specimen is applied to the chromatographic sensor. First, as shown in FIGS. 15A and 16A, a liquid specimen (in FIGS. 15A and 16A, a blood sample S) is applied to the specimen application portion 50 using a tool such as a dispenser or a dropper (or a syringe 54) (Step 1). Then, as shown in FIG. 16B, the liquid specimen permeates and spreads over the entire specimen application region 5 (Step 2). Then, as shown in FIG. 16C, the liquid specimen retained in the specimen application region 5 is developed to the labeling-reagent retaining portion 4 (Step 3). At this time, a labeling-reagent coming into contact with a development tip of the liquid specimen is quickly dissolved, and as shown in FIG. 16D, the dissolved labeling-reagent is developed with the flow of the liquid specimen. During the development of the liquid specimen, an analyte and the labeling-reagent form a complex, and the complex is developed with the flow. The labeling-reagent is swept by the liquid specimen and dissolved. As shown in FIG. 16E, the labeling-reagent is developed in the development flow channel 2 and passes through the reagent-immobilized portion 3. In Step 5, as shown in FIG. 16F, the labeling-reagent is developed to the water absorbing portion 6 and absorbed (Step 6). As such, the labeling-reagent exists with higher concentration in positions closer to the development tip of the liquid specimen. The analyte that can come into contact with the labeling-reagent to form a complex mostly exists in a development front portion in the liquid specimen, while there is little labeling-reagent in the liquid specimen in a development rear portion and only an unreacted analyte is developed.

Thus, for the above-described configuration of the chromatographic sensor, the entire liquid specimen is actually not evaluated by the chromatographic sensor as a result, but the existence or the amount of the analyte in a part of the applied liquid specimen is simply determined. Thus, when the analyte with a high concentration exists in the liquid specimen, the analyte can be sufficiently detected, but when the analyte with a low concentration exists, the analyte can be detected if all the labeling-reagents and the analyte extremely satisfactorily react with each other. However, for the above reason, it is impossible to satisfactorily detect the analyte with the chromatographic sensor having the current configuration, and unfortunately, a region with high sensitivity (a nanomole region or a picomole region to a lower concentration region) of an analyte cannot be accommodated.

As described above, in the conventional configuration, the labeling-reagent cannot be completely dissolved and is not uniformly diffused and developed in the liquid specimen. Thus, when quantitative measurement using the chromatographic sensor is performed, unfortunately, it is impossible to obtain sufficient accuracy and perform measurement with high sensitivity.

Further, since all the sensor components other than the substrate 1 are formed of a liquid permeable material such as glass fiber filter paper or a porous film, the liquid specimen permeates each sensor component and water in the liquid specimen is retained, thereby causing a liquid amount (dead volume) that does not flow out downstream. Thus, in the conventional chromatographic sensor, a larger amount of liquid specimen needs to be applied in view of at least the dead volume due to the water retained by each sensor component. Thus, when the liquid specimen is, for example, blood, it is impossible to measure the blood as a small amount of specimen.

Patent Document 4 reports a biosensor including a space forming portion in which a clearance as a space for the flow by capillarity is formed in a part of a development layer. Herein, the space forming portion is formed such that a space in a specimen application portion is enclosed by a liquid impermeable material, and can retain a certain amount of liquid specimen. However, a labeling-reagent is formed in a part of the development layer and thus the amount of specimen cannot be sufficiently reduced. Also, a dissolution pattern of the labeling-reagent by the development of the liquid specimen is the same as in Patent Documents 1 to 3. Thus, the dissolution and development states of the labeling-reagent in Patent Documents 1 to 3 cannot be improved.

PRIOR ART DOCUMENTS

Patent Documents

Patent Document 1: Japanese Patent No. 2890384
Patent Document 2: Japanese Patent Publication No. 7-78503

Patent Document 3: Japanese Patent No. 2504923
Patent Document 4: Japanese Patent No. 3553045

DISCLOSURE OF THE INVENTION

Problems to be Solved by the Invention

As described above, in Patent Documents 1 to 4, in the biosensor based on an immune reaction, the sensor components other than the substrate 1 are basically made of the liquid permeable material such that the components can communicate with each other by a capillary flow (flow by capillarity).

The inventions in Patent Documents 1 to 4 are achieved in order to easily and quickly analyze the analyte in the liquid specimen using the components made of the construction material and the configurations, and these techniques allow many tests to be conducted in the current medical sites.

However, in the conventional general chromatographic sensor shown in FIGS. 14A to 14C and 16A to 16F, when the liquid specimen is a blood sample S, it is generally necessary that a syringe 54 is used to collect blood, and a large amount of blood sample S is directly applied from the syringe 54, or a tool such as a dispenser or a dropper is used to apply whole blood, or plasma and serum. Thus, application of the specimen to the chromatographic sensor is very complicated, and so simplification of operations in the POCT test for easy and quick measurement is a very important challenge.

Also, in any of the inventions in the patent documents, the labeling-reagent is retained by the liquid permeable material such as a porous material. Thus, the labeling-reagent is quickly dissolved with the development of the liquid specimen, and exists in the development tip with a very high concentration and is developed. However, the retained labeling-reagent cannot be completely dissolved, and several percent to several tens percent of the labeling-reagent remain in a retaining carrier. The amount of remaining labeling-reagent differs depending on biosensors, and thus the amount of labeling-reagent passing through the reagent-immobilized portion is not constant between the biosensors. This causes differences in the degree of coloring even with the same amount of analyte, thereby preventing achievement of quantitative measurement with high accuracy using the biosensor.

Further, the developed labeling-reagent is not diffused over the entire applied liquid specimen to react with the analyte, but flows out with a part of the liquid specimen in the development tip to react with only a part of the analyte. This prevents detection of an analyte with a low concentration, and makes it impossible to perform measurement with high sensitivity that requires detection and quantification of a nano-mole region, a picomole region, and a lower concentration region.

Also, the sensor components other than the substrate 1 are made of the liquid permeable material, and thus water in the developed liquid specimen is retained by each sensor component to cause a loss of specimen (dead volume). Thus, in the chromatographic sensor in which the liquid development serves as bound/free separation (separation between an antigen bound to an antibody and an antigen not bound to an antibody), an excessive amount of liquid specimen needs to be applied for sufficient development (B/F separation). There is no problem when urine in an excessive amount of specimen is a liquid specimen, while for detection of an analyte in blood, blood more than necessary needs to be collected from an upper arm, and this is not an easy and quick test system.

To solve these problems and achieve quantitative measurement of a smaller amount of liquid specimen (a small amount of specimen) with precision, high accuracy, and high sensitivity, it is important and essential to provide a biosensor as an immuno-chromatographic sensor that reduces a dead volume, can dissolve 100% of a labeling-reagent or other reagents, and can cause a reaction of an analyte in the entire liquid specimen.

Also, when a blood sample S is applied as the liquid specimen, a blood cell component (particularly, red blood cell) in blood may prevent check of the result, and the blood cell component sometimes cannot be developed in the development flow channel. Thus, when the conventional chromatographic sensor or biosensor is used, it is necessary to previously remove the blood cell component by centrifugal separation or the like and apply only a serum or plasma component to the specimen application portion, or provide a blood cell filter that can filter the blood cell component between the specimen application region and the development flow channel.

The present invention is achieved in view of the above-described problems, and has an object to provide a biosensor that can satisfactorily retain a certain amount of blood as a liquid specimen without using a dispenser, a dropper, or a syringe, also completely dissolve a labeling-reagent or other reagents, significantly reduce the amount of applied blood, and further allow the blood in which the labeling-reagent is uniformly dissolved to satisfactorily flow into a development flow channel. This can provide the biosensor as an immuno-chromatographic sensor with precision, high accuracy, and high sensitivity based on an immune reaction that can increase measurement accuracy, also keep convenience in the conventional immuno-chromatographic sensor, achieve measurements performed anywhere at any time by anybody, and allow measurement with a small amount of liquid specimen such as blood.

Means for Solving the Problems

To solve the above-described problems, the present invention provides a biosensor determining whether an analyte is present or not in a liquid specimen, or measuring a concentration of the analyte in the liquid specimen, which comprising: a specimen application portion to which the liquid specimen is applied; a reaction reagent reacting with the liquid specimen; and a development flow channel in which the liquid specimen mixed with the reaction reagent or the liquid specimen having reacted with the reaction reagent is developed, wherein: the specimen application portion is configured such that an application space is enclosed by a space-forming member made of a liquid impermeable material; the reaction reagent is retained in a position of the space-forming member facing the application space in the specimen application portion so that the reaction reagent can be dissolved into the liquid specimen applied to the application space; the development flow channel is made of a material such that the liquid specimen and the reaction reagent in the specimen application portion can be developed by a capillary force; and a measurement region is provided in a part of the development flow channel.

With this configuration, the space-forming member that forms the application space in the specimen application portion is made of the liquid impermeable material. Thus, water in the liquid specimen retained by the specimen application portion is not retained by the specimen application portion, and the liquid specimen can be developed in the development flow channel to a downstream region in a development direction without remaining. This eliminates a dead volume remaining in the specimen application portion, thereby significantly reducing the liquid specimen required for measurement.

The liquid impermeable material refers to a material into which liquids does not permeate, and includes, for example, synthetic resin materials such as ABS, polystyrene or polyvinyl chloride, metal, or glass. The liquid impermeable material also includes a material such as paper into which liquids can permeate but which has a surface coated with resin or a film or made water repellent to prevent permeation of liquids.

Also, the development flow channel may be made of any material or have any configuration such that liquids can be developed by a capillary force. The development flow channel includes, for example, a passage formed of a small space, a small passage having nano pillars, or any liquid permeable material such as a porous film or glass fiber filter paper. Preferably, the development flow channel is formed of a single layer, and any material may be used such as a membrane filter typified by cellulose nitrate, glass fiber filter paper, cellulose filter paper, or a small passage formed of a liquid impermeable material.

Also, according to the above-described configuration, the reaction reagent is retained in the application space formed by the space-forming member made of the liquid impermeable material. Thus, the retained reaction reagent does not remain in or is not adsorbed by a carrying material, but the reaction reagent can be completely dissolved. Thus, the degree of dissolution of the reaction reagent becomes substantially constant to eliminate a sensitivity difference as in the conventional cases such as "high sensitivity with a large amount of dissolved reaction reagent" or "low sensitivity with a small amount of dissolved reaction reagent", thereby stabilizing measurement results. This can obtain measurement results with precision, high accuracy, and high sensitivity.

The reaction reagent includes, for example, a modifier that reacts with a liquid specimen, any reagent required for an enzyme reaction, or a labeling-reagent containing a tracer that can specifically react with an analyte and an immobilized-reagent. The tracer herein refers to a ligand portion and a detectable labeling portion bound to the ligand portion. The detectable labels may be any of various kinds of detectable labels. In a preferred aspect of the present invention, various chromogens, for example, fluorescent substances, absorbent dyes or light emitting substance, insoluble granular carrier, for example, metal colloid or latex particles may be used. Enzymes may be used. The "liquid specimen having reacted with the reaction reagent" refers to a state where an analyte in the liquid specimen reacts with a tracer or a state where any component in the liquid specimen reacts with any reagent in the reaction reagent.

The measurement region may be one or more regions. Further, the development flow channel may be made of any material or have any configuration such that liquids can be developed by a capillary force. The development flow channel includes, for example, a passage formed of a small space, a small passage having nano pillars, or any liquid permeable material such as a porous film or glass fiber filter paper. Preferably, the development flow channel is formed of a single layer.

Also, in the biosensor of the present invention, the reaction reagent is provided in a position not in a surface on an extension of the development flow channel in the specimen application portion. In the biosensor of the present invention, the development flow channel is placed along a surface of a substrate as a support, and the space-forming member has an upper surface having a back side spaced apart from and facing the surface of the substrate, and the reaction reagent is retained on the back side of the upper surface in the space-forming member.

As such, the reagent is provided in the position not in the surface on the extension of the development flow channel in the specimen application portion, or retained on the back side of the upper surface spaced apart from and facing the surface of the substrate in the space-forming member. Thus, as compared with the case where the reaction reagent is provided in the surface on the extension of the development flow channel in the specimen application portion, the reaction reagent is introduced into the development flow channel in a state where the reaction reagent is more uniformly dissolved into the liquid specimen applied to the specimen application portion, thereby obtaining measurement results with higher precision, higher accuracy, and higher sensitivity. Specifically, when the reaction reagent is provided in the surface on the extension of the development flow channel in the specimen application portion, the position where the reaction reagent is retained is brought into contact with or brought extremely close to the development flow channel. Thus, a nonuniform liquid specimen immediately after the reaction reagent is dissolved into the liquid specimen may be introduced into the development flow channel to reduce accuracy or sensitivity. The above-described configuration can prevent such defects.

The position not on the extension of the development flow channel along a thickness direction of the development flow channel in the specimen application portion refers to any surface other than a bottom surface located in flush with the development flow channel. For example, when the development flow channel is provided along a bottom surface of the specimen application portion, the position refers to the back side of the upper surface located upward of the bottom surface of the space-forming member such as a cover that encloses the specimen application portion, or a side surface extending upward from the bottom surface.

In the present invention, an auxiliary substrate that functions as a spacer that defines a thickness of the application space is provided on the substrate.

With this configuration, the volume that can be retained in the application space can be defined not only by a length and a width of the application space but also a thickness of the auxiliary substrate that functions as a spacer. A biosensor can be achieved that can retain various volumes by changing the thickness of the auxiliary substrate. This can further simplify the structure of the biosensor, and minimize variations in the degree of reaction due to variations in the structure of the biosensor, thereby achieving measurement with higher accuracy.

In the biosensor of the present invention, an air hole that facilitates suction of the liquid specimen into the application space is formed in the space-forming member.

With this configuration, the air hole that facilitates suction of the liquid specimen into the application space is formed in the space-forming member, thereby increasing the capillary force in the application space. Thus, the liquid specimen can be quickly sipped into the application space simultaneously with the application of the liquid specimen such as blood to the application space, and a certain amount of liquid specimen can be retained in the application space more reliably and instantly, thereby minimizing a shortage of the applied liquid specimen.

In the biosensor of the present invention, the measurement region includes a reagent-immobilized portion in which a reagent is immobilized as an immobilized-reagent that can behave a specific reaction with an analyte or a reaction reagent.

In the biosensor of the present invention, the reaction reagent contains a labeling-reagent that can specifically react with the analyte or the immobilized-reagent.

With this configuration, the reaction reagent contains the labeling-reagent, and thus when the liquid specimen comes into contact with the reaction reagent, the labeling-reagent is quickly dissolved or hydrated and can react with the analyte in the liquid specimen. The labeling-reagent and the liquid specimen are developed in the development flow channel after the reaction, and thus the labeling-reagent can reliably react with the analyte. Also, the liquid specimen having reacted passes through the reagent-immobilized portion, and thus the degree of reaction in the reagent-immobilized portion can be made uniform, and measurement variations depending on the degree of reaction are improved, thereby achieving measurement with higher accuracy.

In the biosensor of the present invention, the labeling-reagent is obtained by labeling a reagent that can specifically react with the analyte or the immobilized-reagent with an insoluble granular marker.

In the biosensor of the present invention, the insoluble granular marker is selected from the group including a colored polymer bead, a metal, an alloy, and a polymer dye particle.

In the biosensor of the present invention, the specific reaction is an antigen-antibody reaction.

With this configuration, the biosensor using the specific reaction such as the antigen-antibody reaction can reduce a loss of liquid specimen in the specimen application portion, thereby allowing measurement of a small amount of liquid specimen. The carried reaction reagent such as the labeling-reagent can be completely dissolved and flown out, and the reaction reagent can be satisfactorily diffused over the entire liquid specimen for a reaction.

In the biosensor of the present invention, the reaction reagent is a reagent other than a labeling-reagent.

With this configuration, the reaction reagent is a reagent other than the labeling-reagent. Thus, for example, quantification of hemoglobin can be performed in a reaction system that does not require a tracer, for example, measurement of HbA1c. Also, when the labeling-reagent is an enzyme, a substrate reagent for an enzyme reaction generally needs to be later developed, but this need can be eliminated, thereby achieving accommodation of various reaction systems.

The biosensor of the present invention includes a liquid impermeable sheet that covers a surface of the development flow channel.

With this configuration, the surface of the development flow channel is covered with the liquid impermeable sheet. Thus, the liquid specimen developed from the specimen application portion does not evaporate and dry from the surface of the development flow channel, but can be developed in the development flow channel to the chromatography downstream region. Also, bound/free separation (separation between a complex formed by a specific binding reaction and an unreacted substance) is reliably performed in the reagent-immobilized portion, thereby allowing measurement with higher precision and achieving measurement with higher sensitivity and higher accuracy.

In the biosensor of the present invention, the measurement region includes a reagent-immobilized portion in which a reagent is immobilized as an immobilized-reagent that can behave a specific reaction with an analyte or a reaction reagent; and the liquid impermeable sheet covers a range from a part of or neighborhood of the application space in the specimen application portion to at least the reagent-immobilized portion.

With this configuration, a surface of the position where the reagent-immobilized portion is provided in the development flow channel is covered with the liquid impermeable sheet. Thus, the liquid specimen developed from the application space of the specimen application portion is satisfactorily developed without evaporating from the surface of the reagent-immobilized portion in the development flow channel.

In the biosensor of the present invention, the liquid impermeable sheet does not cover the development flow channel in a downstream end of the development flow channel.

With this configuration, in the downstream end of the development flow channel, that is, the position downstream of the reagent-immobilized portion in the development flow channel, which is not covered with the liquid impermeable sheet, the developed liquid evaporates and dries. Thus, development from a chromatography upstream region to a chromatography downstream region of the liquid specimen is facilitated, and also bound/free separation in the reagent-immobilized portion is reliably performed, thereby allowing measurement with high precision and achieving measurement with higher sensitivity and higher accuracy.

In the biosensor of the present invention, both side surfaces along a development direction of the development flow channel are covered or sealed.

With this configuration, the both side surfaces along the development direction of the development flow channel are covered or sealed. This can prevent evaporation and drying of the liquid specimen from the both side surfaces, and facilitate the development of the liquid specimen in the direction of the chromatography downstream region, otherwise the development tends to escape to both sides of the development flow channel. This can make uniform the development of the liquid specimen and minimize variations in the degree of reaction due to nonuniform development of the liquid specimen, thereby achieving measurement with higher accuracy.

In the biosensor of the present invention, the liquid specimen is a blood sample.

In the biosensor of the present invention, the reaction reagent contains a cell component shrinkage agent or a mixed reagent containing a cell component shrinkage agent, the cell component shrinkage agent reacts with a blood cell component in the blood sample, and the blood sample is developed in the development flow channel in a state where the blood cell component has been or is being shrunk.

With this configuration of the present invention, the reaction reagent carries the cell component shrinkage agent or a mixed reagent containing the cell component shrinkage agent. Thus, the blood cell component in the blood sample is quickly shrunk when coming into contact with the cell component shrinkage agent as the reaction reagent, and the size of the blood cell component is made uniform. Thus, a nonuniform development state of the blood sample due to blood cell components having nonuniform sizes can be made uniform. This can make the degree of reaction uniform and improve measurement variations, thereby achieving measurement with higher accuracy.

In the biosensor of the present invention, blood from a fingertip can be sipped into the application space in the specimen application portion by a capillary force.

In the biosensor of the present invention, the reaction reagent and an immobilized-reagent in a dry state are retained and immobilized in the biosensor, and are dissolved or hydrated into the liquid specimen.

With this configuration, the reaction reagent and the immobilized-reagent are both in a dry state, and the biosensor is a dry analysis element. Thus, the biosensor can be portable and conveniently stored, thereby allowing measurement anywhere at any time by anyone.

In the biosensor of the present invention, the reaction reagent in a solution state is applied to an inner surface of the space-forming member and then dried, and the immobilized-reagent in a solution state is applied to the development flow channel and then dried.

In the biosensor of the present invention, a suction capacity of the application space in the specimen application portion is 10 µl or less.

With this configuration, as compared with a conventional chromatographic sensor, the amount of specimen can be significantly reduced, and satisfactory qualification or quantification can be performed with an extremely small amount of blood sample from a fingertip or the like.

In the biosensor of the present invention, the application space is configured to be enclosed by the space-forming member made of a liquid impermeable material, an upstream portion of the development flow channel enters the application space from one end of the application space, and an entering position in the upstream end of the development flow channel is located on a deeper side in a suction direction than an opening for sipping the liquid specimen formed on the other end of the application space.

With this configuration, a certain small amount of liquid specimen can be retained only by an operation of applying an appropriate amount of liquid specimen without requiring a tool such as a dispenser for applying a certain amount of liquid specimen such as a blood sample or a water absorbing pad for retaining the applied blood, and also a small amount of liquid specimen can be developed and analyzed. The upstream end of the development flow channel enters the application space only to the position on the deeper side in the suction direction than the opening for sipping the liquid specimen in the application space. Thus, when the liquid specimen is sipped through the opening, only the reaction reagent is first dissolved and mixed into the liquid specimen. Then, the liquid specimen into which the reaction reagent has been already satisfactorily dissolved and mixed or reacted flows into the upstream end of the development flow channel located on the deeper side in the suction direction than the opening, that is, the downstream side in the development direction, and the liquid specimen is developed. Thus, the liquid specimen into which the reaction reagent is uniformly dissolved can satisfactorily flow into the development flow channel, thereby allowing qualification or quantification with high accuracy.

In the biosensor of the present invention, the development flow channel is supported on the substrate, the application space is formed as a required suction space by one end of the substrate corresponding to the upstream end of the development flow channel and the space-forming member covering one end of the substrate, the development flow channel has a predetermined thickness, and in the application space, an auxiliary substrate is provided that is placed to eliminate or reduce unevenness corresponding to the thickness of the development flow channel formed between the upstream end of the development flow channel entering the application space and the substrate, thereby reducing the thickness of the application space and retaining a capillary force.

With this configuration, the auxiliary substrate is provided, and thus the specimen application portion formed by the space-forming member is retained so that the specimen application portion satisfactorily sips the liquid specimen such as a blood sample with a capillary force, thereby allowing the liquid specimen to be satisfactorily sipped and preventing a shortage of suction amount.

In the biosensor of the present invention, the development flow channel is supported on the substrate, the application space is formed as a required suction space by an auxiliary substrate that is formed of one end of the substrate corresponding to the upstream end of the development flow channel and defines the thickness of the specimen application portion, and the space-forming member that faces the substrate and covers one end of the substrate.

With this configuration, the volume that can be retained in the application space can be defined not only by a length and a width of the application space but also the thickness of the auxiliary substrate. A biosensor can be achieved that can retain various volumes by changing the thickness of the auxiliary substrate. This can further simplify the structure of the biosensor, and minimize variations in the degree of reaction due to variations in the structure of the biosensor, thereby achieving measurement with higher accuracy.

Advantage of the Invention

As described above, according to the present invention, the specimen application portion is configured such that the application space is enclosed by the space-forming member made of the liquid impermeable material. Thus, the liquid specimen can be developed in the development flow channel without water in liquid specimen being retained by the specimen application portion. This can minimize an undeveloped specimen, that is, a loss of specimen (dead volume) caused by water in the applied liquid specimen being retained by the construction material as in the conventional case, thereby significantly reducing the amount of specimen (amount of liquid specimen) as compared with the conventional chromatographic sensor. Thus, the blood from a fingertip can be sipped into the application space in the specimen application portion by a capillary force, and in this case, the suction capacity of the application space, that is, a required amount of blood can be 10 µl or less.

The reaction reagent is retained by the liquid impermeable space-forming member. Thus, the reaction reagent can be completely dissolved without remaining in or being adsorbed by the space-forming member as a retaining portion. Thus, the degree of dissolution of the reaction reagent becomes always constant. Also, the reaction reagent comes into contact with the liquid specimen and is dissolved into the application space, and spreads over and reacts with the entire liquid specimen, and then can be developed in the development flow channel, thereby preventing remaining of the reaction reagent and development of the liquid specimen that has not reacted with the reaction reagent.

As such, the reaction reagent can be 100% dissolved, and development of the unreacted liquid specimen can be prevented. Also, the application space is enclosed by the space-forming member made of the liquid impermeable material, thereby providing a biosensor that can perform easy and quick measurement with higher precision, higher accuracy, and higher sensitivity.

The reaction reagent is provided in the position not in the surface on the extension of the development flow channel in the specimen application portion, or retained on the back side of the upper surface spaced apart from and facing the surface of the substrate in the space-forming member. Thus, the reaction reagent is introduced into the development flow channel in a state where the reaction reagent is more uniformly dissolved into the liquid specimen applied to the application space in the specimen application portion, thereby obtaining measurement results with higher precision, higher accuracy, and higher sensitivity.

The auxiliary substrate that functions as the spacer that defines the thickness of the application space is provided on the substrate. Thus, the volume of the liquid specimen such as blood that can be retained in the application space can be easily obtained simply by changing the thickness of the auxiliary substrate that functions as the spacer. This can further simplify the structure of the biosensor, and minimize variations in the degree of reaction due to variations in the structure of the biosensor, thereby achieving measurement with higher accuracy.

The air hole that facilitates suction of the liquid specimen into the application space is formed in the space-forming member in the biosensor of the present invention. Thus, the liquid specimen can be quickly sipped into the application space simultaneously with the application of the liquid specimen to the application space, and a certain amount of liquid specimen can be retained more reliably and instantly, thereby minimizing the shortage of the applied liquid specimen.

The reaction reagent contains the labeling-reagent that can specifically react with the analyte or the immobilized-reagent. Thus, the labeling-reagent and the liquid specimen are developed in the development flow channel after the reaction, and thus the labeling-reagent can reliably react with the analyte. Also, the degree of reaction in the reagent-immobilized portion can be made uniform. Thus, measurement variations depending on the degree of reaction are improved, thereby achieving measurement with higher accuracy.

The surface of the development flow channel is covered with the liquid impermeable sheet. Thus, the liquid specimen does not evaporate and dry from the surface of the development flow channel, but can be developed in the development flow channel to the chromatography downstream region. Also, bound/free separation is reliably performed in the reagent-immobilized portion, thereby allowing measurement with higher precision and achieving measurement with higher sensitivity and higher accuracy.

The both side surfaces along the development direction of the development flow channel are sealed. This can facilitate the development of the liquid specimen in the direction of the chromatography downstream region, otherwise the development tends to escape to the both sides of the development flow channel. This can make uniform the development of the liquid specimen, and minimize variations in the degree of reaction due to nonuniform development of the liquid specimen.

When the liquid specimen is blood, the reaction reagent contains a cell component shrinkage agent or a mixed reagent containing the cell component shrinkage agent. Thus, a blood cell component in the blood is quickly shrunk when coming into contact with the cell component shrinkage agent as the reaction reagent, and the size of the blood cell component is made uniform. Thus, the development state of the blood can be made uniform, thereby achieving measurement with higher accuracy.

According to the present invention, the reaction reagent is carried in the application space that can sip and retain the liquid specimen by a capillary force. The development flow channel is provided so that the upstream end enters the application space only to the position on the deeper side in the suction direction than the opening for sipping the blood liquid specimen in the application space. Thus, when the liquid specimen such as the blood sample is applied and sipped into the application space, the reaction reagent is satisfactorily dissolved into the liquid specimen, and then the liquid specimen flows into the upstream end of the development flow channel and is developed. Thus, the liquid specimen into which the reaction reagent is uniformly dissolved can satisfactorily flow into the development flow channel, thereby allowing qualification or quantification with high accuracy and allowing measurement with high sensitivity.

In the application space, the auxiliary substrate is provided that is placed to eliminate or reduce the unevenness corresponding to the thickness of the development flow channel formed between the upstream end of the development flow channel entering the application space and the substrate, thereby reducing the thickness of the application space and retaining a capillary force. Thus, the capillary force for sipping the liquid specimen satisfactorily acts in the application space, and thus the liquid specimen can be satisfactorily sipped, thereby improving accuracy in qualification or quantification.

The development flow channel is supported on the substrate, and the application space is formed as a required suction space by an auxiliary substrate that is formed of one end of the substrate corresponding to the upstream end of the development flow channel and defines the thickness of the application space, and the space-forming member that faces the substrate and covers one end of the substrate. Thus, the volume of the blood sample that can be retained in the application space can be easily obtained only by changing the thickness of the auxiliary substrate. This can further simplify the structure of the biosensor, and minimize variations in the degree of reaction due to variations in the structure of the biosensor, thereby achieving measurement with higher accuracy.

BEST MODE FOR CARRYING OUT THE INVENTION

Embodiments of a biosensor according to the present invention will be specifically described below with reference to the accompanying drawings. The following embodiments are merely exemplary and the present invention is not always limited to the following embodiments. In the embodiments, a test substance is substantially the same as an analyte.

Figure 1A:
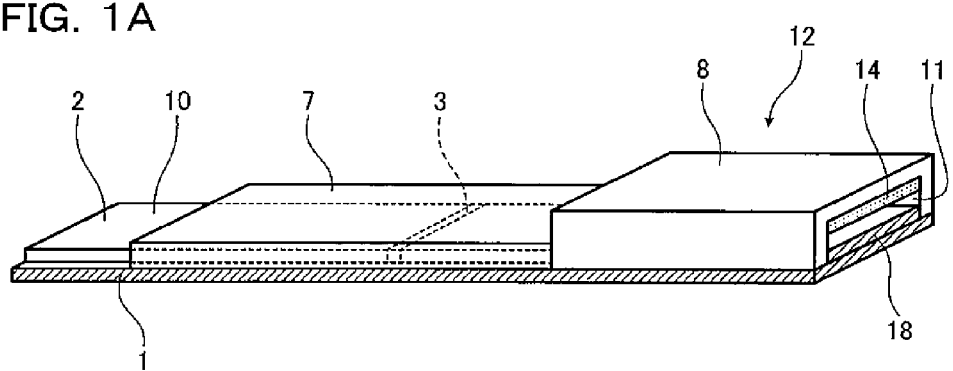
FIG. 1A is a perspective view of a biosensor according to a first embodiment of the present invention.
Figure 1B:
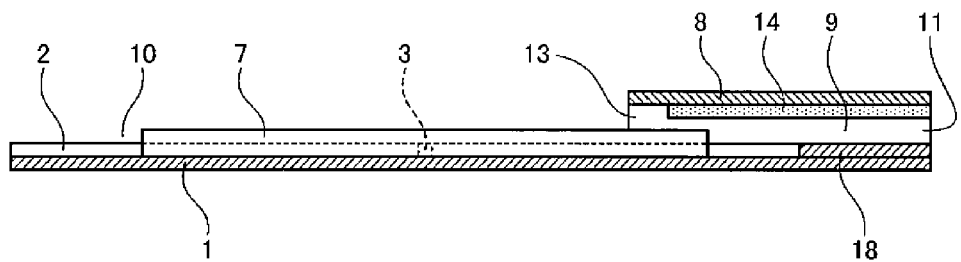
FIG. 1B is a vertical sectional view of the biosensor.
Figure 1C:
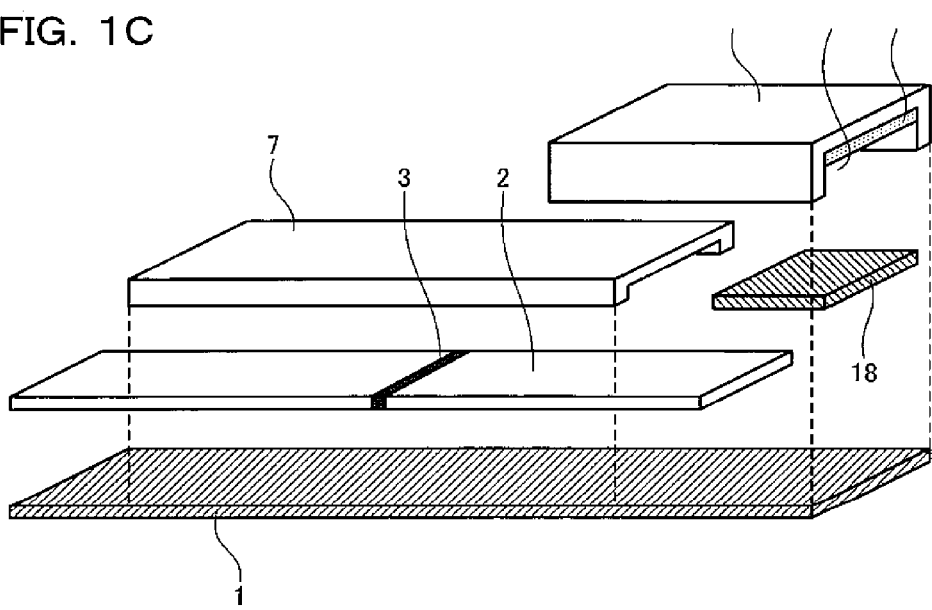
FIG. 1C is an exploded perspective view of the biosensor.

FIGS. 1A, 1B and 1C show a configuration of a biosensor according to a first embodiment of the present invention, FIG. 1A is a perspective view of the biosensor, FIG. 1B is a vertical sectional view of the biosensor, and FIG. 1C is an exploded perspective view of the biosensor.

As shown in FIGS. 1A to 1C, the biosensor includes a specimen application portion 12 (application space 9) to which a liquid specimen is applied, a reaction reagent 14 that reacts with the liquid specimen, a development flow channel 2 in which a liquid specimen mixed with the reaction reagent 14 or a liquid specimen having reacted with the reaction reagent 14 is developed, and a substrate 1 as a support that supports the specimen application portion 12 and the development flow channel 2, and measures presence and absence or a concentration of an analyte in the liquid specimen using immuno-chromatography. The specimen application portion 12 is configured such that a small application space 9 is enclosed by a space-forming member 8 made of a liquid impermeable material, and the reaction reagent 14 containing a tracer (hereinafter referred to as a labeling-reagent) is retained in a position facing the application space 9 of the space-forming member 8 that form small space in the specimen application portion 12 so that the reaction reagent 14 can be dissolved into the liquid specimen applied to the application space 9. The tracer includes a ligand portion and a detectable labeling portion bound to the ligand portion.

The reaction reagent 14 containing the tracer (labeling-reagent) is retained in a position not on an upper surface (a surface on an extension of the development flow channel 2 in the specimen application portion 12) of the substrate 1 corresponding to a bottom surface of the application space 9 into which an upstream region in a chromatography development direction of the development flow channel 2 protrudes in the specimen application portion 12, without contact with the development flow channel 2 or the substrate 1. In this embodiment, the reaction reagent 14 is retained on a back side of an upper surface of the space-forming member 8. The back side is spaced a predetermined distance apart from and faces the upper surface of the substrate 1 on which the development flow channel 2 is provided.

When the liquid specimen to be measured is plasma or serum that does not contain a cell component such as a blood cell, the reaction reagent 14 contains a labeling-reagent but does not contain a cell component shrinkage agent that shrinks a cell component. On the other hand, when the liquid specimen to be measured is whole blood that contains a cell component such as a blood cell, the reaction reagent 14 contains a labeling-reagent and a cell component shrinkage agent.

In a part of the development flow channel 2, a reagent-immobilized portion 3 is provided in which specific protein is immobilized. The reagent-immobilized portion 3 is also used as a measurement region. A liquid impermeable sheet 7 made of a liquid impermeable material covers a surface of the development flow channel 2 from a chromatography upstream region to a chromatography downstream region including at least the reagent-immobilized portion 3. The liquid impermeable sheet 7 does not cover an opened portion 10 in a downstream end region (also referred to as a chromatography downstream end) in a chromatography development direction. In the chromatography upstream region, a specimen application portion 12 is provided configured such that the small application space 9 is enclosed by the space-forming member 8 made of the liquid impermeable material. As shown in FIG. 1B, the application space 9 is a space corresponding to a chromatography upstream end for sipping a certain amount of liquid specimen (sips a certain amount of liquid specimen by capillarity in this embodiment), and a tip of the application space 9 is an opening 11 for supplying the liquid specimen to the biosensor.

Also in this embodiment, an auxiliary substrate 18 (made of the same material as that of the substrate 1, and made of a liquid impermeable material as described later) that functions as a spacer is placed only in the chromatography upstream region of the biosensor on the substrate 1 that forms a bottom surface (support) of the biosensor. An end of the chromatography upstream region in the development flow channel 2 is located only to a position on a deeper side in a suction direction than the opening 11 in the application space 9, that is, to a downstream position in the chromatography development direction. The development flow channel 2 is not provided in a region from the upstream end of the development flow channel 2 to the opening 11. The auxiliary substrate 18 eliminates unevenness on the bottom surface of the application space 9 and also has a function of adjusting a thickness (vertical thickness) of the application space 9 so as to satisfactorily sip the liquid specimen in a position continuous with the opening 11 by capillarity. The auxiliary substrate 18 is made of a liquid impermeable material, and preferably has the same thickness as the development flow channel 2 to eliminate the unevenness from the development flow channel 2. However, not limited to this, the auxiliary substrate 18 may have a thickness simply reducing the unevenness from the development flow channel 2, and may be made of any material and have any thickness. Further, the unevenness may still exist if the application space 9 has a small thickness in this position and thus a capillary force can be retained. The auxiliary substrate 18 is not always separated from the substrate 1, but a thick portion corresponding to the auxiliary substrate 18 may be integrally formed with the substrate 1. The thick portion corresponding to the auxiliary substrate 18 is integrally formed with the substrate 1, or a separate auxiliary substrate 18 is joined to the substrate 1 with high accuracy. Thus, when the space-forming member 8 is mounted on the substrate 1 to form the application space 9, the space-forming member 8 can be mounted on the substrate 1 without a warp, advantageously improving assembly accuracy.

Next, with reference to FIGS. 2A, 2B, 2C, 2D and 2E, a development state of the liquid specimen on the biosensor will be described. FIGS. 2A to 2E are sectional views showing the development state of the liquid specimen in the biosensor according to the embodiment of the present invention when the liquid specimen is applied to the biosensor.

Figure 2A:
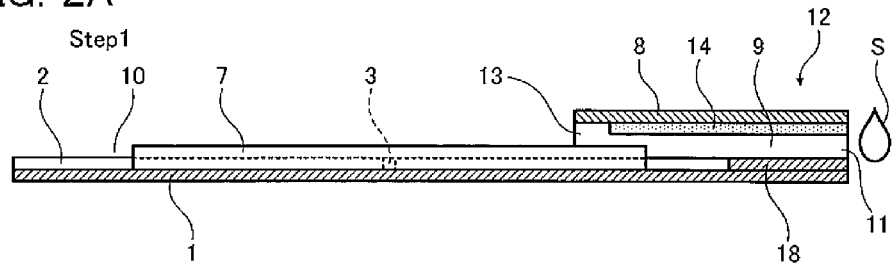
FIG. 2A is a sectional view showing a development state of a liquid specimen in the biosensor when the liquid specimen is applied to the biosensor.
Figure 2B:
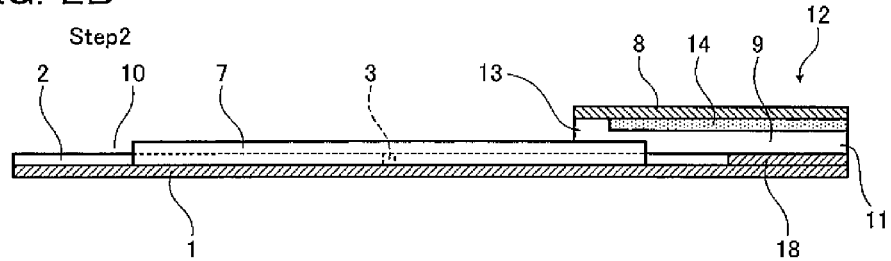
FIG. 2B is a sectional view showing the development state of the liquid specimen in the biosensor when the liquid specimen is applied to the biosensor.
Figure 2C:
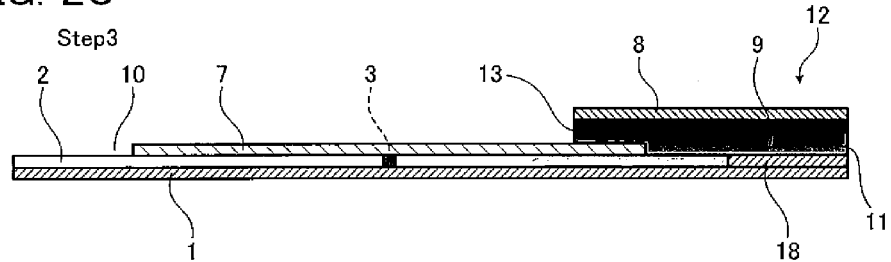
FIG. 2C is a sectional view showing the development state of the liquid specimen in the biosensor when the liquid specimen is applied to the biosensor.

As shown in FIG. 2A, when a liquid specimen such as a blood sample S is dropped (applied) to the opening 11 in the specimen application portion 12 (Step 1), as shown in FIG. 2B, a certain amount of liquid specimen is sipped into the application space 9 by capillarity, and the application space 9 is filled with the liquid specimen (Step 2). When the liquid specimen is sipped into the application space 9, a reagent (a labeling-reagent, or a labeling-reagent and a cell component shrinkage agent) of the reaction reagent 14 comes into contact with the liquid specimen, and starts to be quickly dissolved. When the application space 9 is filled with the liquid specimen, the dissolved labeling-reagent, or the labeling-reagent and the cell component shrinkage agent (hereinafter simply referred to as labeling-reagent or the like) react with the liquid specimen and is diffused in the entire application space 9, and as shown in FIG. 2C, the liquid specimen is developed in the development flow channel 2 (Step 3).

Figure 2D:
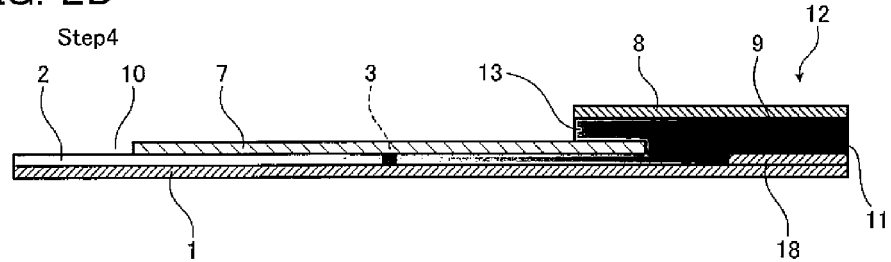
FIG. 2D is a sectional view showing the development state of the liquid specimen in the biosensor when the liquid specimen is applied to the biosensor.
Figure 2E:
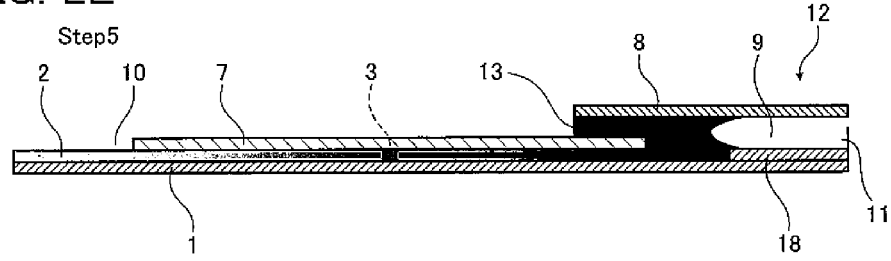
FIG. 2E is a sectional view showing the development state of the liquid specimen in the biosensor when the liquid specimen is applied to the biosensor.

The liquid specimen developed in the development flow channel 2 is developed while reacting with the labeling-reagent or the like. As shown in FIG. 2D, the liquid specimen reaches and then passes through the reagent-immobilized portion 3 (Step 4). When the liquid specimen reaches the reagent-immobilized portion 3, and there is an analyte in the liquid specimen, a specific reaction is performed between the labeling-reagent, the analyte, and an immobilized-reagent. A color reaction caused by the labeling-reagent occurs in the reagent-immobilized portion 3. The liquid specimen further developed in the development flow channel 2 is prevented from water evaporation from a surface by the action of the liquid impermeable sheet 7 in a region of the development flow channel 2 covered with the liquid impermeable sheet 7, and water evaporation starts after the liquid specimen reaches the opened portion 10 that is not covered with the liquid impermeable sheet 7 (see FIG. 2E). This dry process helps development of the liquid specimen, and facilitates development of the liquid specimen from the specimen application portion 12 to the opened portion 10. The specimen application portion 12 is a small space made of a liquid impermeable material, and the liquid specimen is not retained in the small space but developed in the chromatography downstream direction by the development and the movement of the liquid (Step 5). The reaction of the labeling-reagent having appeared in the reagent-immobilized portion 3 through the steps can be visually checked or detected using a measurement device. This allows checking the presence and absence or the concentration of the analyte in the liquid specimen.

The development flow channel 2 shown herein is a passage made of any material such that a liquid can be developed by a capillary force (force caused by capillarity), and in which the liquid specimen can be developed. The development flow channel 2 may be made of any porous material such as filter paper, nonwoven fabric, membrane, fabric, and glass fiber as long as the material is wet with the liquid specimen and can form a passage for development of the liquid specimen. The passage may be formed of a hollow capillary, and such a hollow capillary may be made of a resin material or the like.

The labeling-reagent is obtained by labeling an antibody with a marker such as a gold colloid and is used as a detector of binding in the reagent-immobilized portion 3. The gold colloid is merely exemplary and any marker may be selected when necessary. For example, metal or nonmetal colloid particles, enzymes, proteins, coloring matters, fluorescent dyes, and dye particles such as latex may be used.

Further, any antibodies may be used for the reagent-immobilized portion 3 as long as a complex of the labeling-reagent and the test substance can be formed. Thus, epitopes and affinities for the test substance may be the same or different from each other. Alternatively, the two antibodies may have different affinities but have the same epitope.

In the configuration of the biosensor shown in FIGS. 1A to 1C and 2A to 2E, the reagent-immobilized portion 3 is provided only at one point. The reagent-immobilized portions do not always have to be provided at one point. At least one point can be freely selected depending on the purpose. Further, the shape of the reagent-immobilized portion 3 on the development flow channel 2 does not always have to be linear and the reagent-immobilized portion may be freely shaped like a spot, a character, or a key. When a plurality of reagent-immobilized portions are set, various positional relationships may be set such that the reagent-immobilized portions are spatially separated from each other or are in contact with each other like a single line.

A liquid impermeable sheet material 7 that covers the development flow channel 2 is composed of, for example, transparent PET tape. The liquid impermeable sheet material 7 tightly covers the development flow channel 2 other than a portion connecting to the application space 9 serving as the specimen application portion and a downstream end for receiving the liquid specimen.

The development flow channel 2 is covered with the liquid impermeable sheet material 7 thus, so that a portion outside the specimen application portion 12 (application space 9) can be protected from dropping and contamination from the outside. Further, it is possible to prevent the developing liquid specimen from evaporating during the development of the liquid specimen, surely pass the liquid specimen through the reagent-immobilized portion 3 that serves as a reaction portion on the development flow channel 2, and allow the reagent-immobilized portions 3 to efficiently react with the test substance in the liquid specimen. In this case, the contamination from the outside refers to that the liquid specimen accidentally comes into contact with the reaction portions on the development flow channel 2 or an examinee directly touches the development flow channel 2 by hand or the like. The liquid impermeable sheet material 7 covering the development flow channel 2 is preferably made of transparent materials. A portion covering the reagent-immobilized portion 3 is a signal measuring portion and is thus preferably at least in a light transmissive state.

Figure 3A:
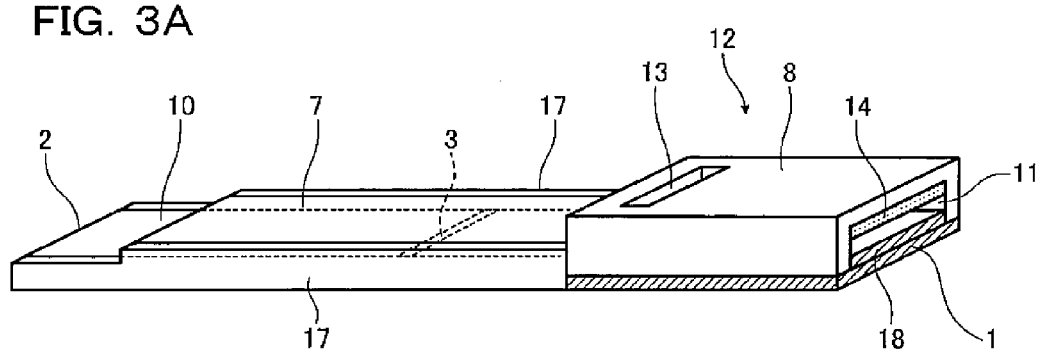
FIG. 3A is a perspective view of a biosensor according to a variant of the first embodiment.
Figure 3B:
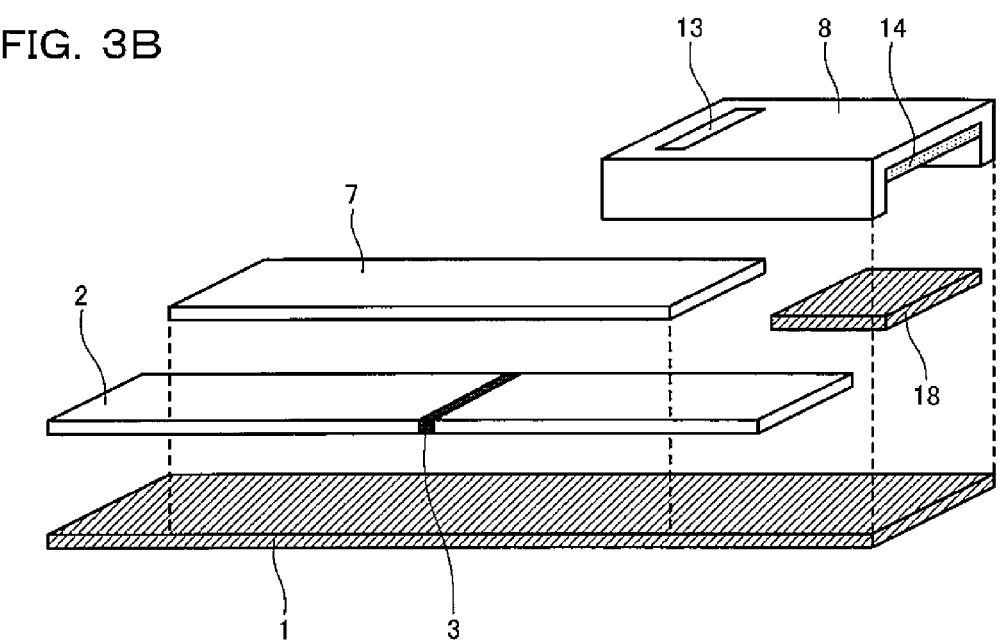
FIG. 3B is an exploded perspective view of the biosensor.
Figure 3C:
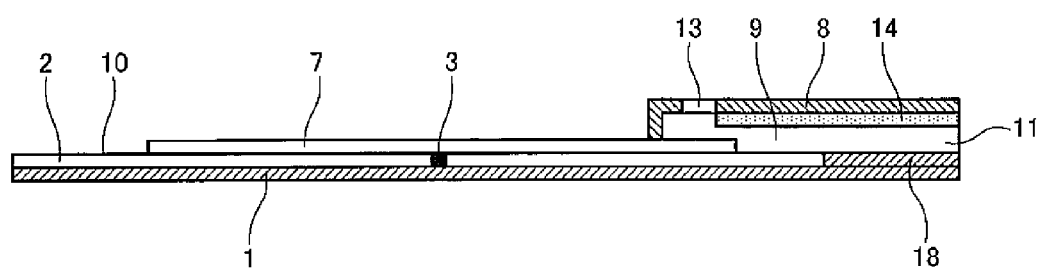
FIG. 3C is a vertical sectional view of the biosensor.

For measurement with higher accuracy, the upper surface and side surfaces of the development flow channel 2 may be tightly sealed particularly including the reagent-immobilized portion 3, and the side surfaces parallel to the development direction of the liquid specimen may be tightly sealed in a similar manner. Thus, the upper surface and also the both side surfaces of the development flow channel 2 are covered with the liquid impermeable sheet material 7. This can prevent evaporation and drying of the liquid specimen from the both side surfaces, and facilitate the development of the liquid specimen in the direction of the chromatography downstream region, otherwise the development tends to escape to both sides of the development flow channel 2. Instead that the liquid impermeable sheet material 7 covers the both side surfaces, as shown in FIG. 3A, the both side surfaces may be sealed (in FIG. 3A, the both sides of the development flow channel 2 and the both side surfaces of the substrate 1 are also sealed, but not limited to this). As a sealing method, a sealer 17 may be applied or filled, but not limited to this. In a production process of the development flow channel 2, laser scanning and melting or laser cutting can seal hole portions in the both side surfaces simultaneously with cutting. Also, as shown in FIGS. 3A, 3B and 3C, an air hole 13 for facilitating the capillary force to the application space 9 may be opened in the upper surface instead of the side surface at one end of the space-forming member 8 forming the application space 9.

The substrate 1 is composed of a liquid impermeable sheet material such as a PET film, and may be transparent, translucent, or opaque. For example, when an optical detector is used, a transparent material is preferably used for measuring a transmitted light, and an opaque material is preferably used for measuring a reflected light. The substrate 1 may be made of synthetic resin materials such as ABS, polystyrene, or polyvinyl chloride, and liquid impermeable materials such as a metal or a glass.

The space-forming member 8 made of the liquid impermeable material that forms the application space 9 in the specimen application portion 12 sips and retains a certain amount of liquid specimen. The space-forming member 8 also provides protection against contamination by the liquid specimen to the outside when the biosensor is handled after the liquid specimen is applied. The space-forming member 8 may be synthetic resin materials such as ABS, polystyrene, or polyvinyl chloride, and liquid impermeable materials such as a metal or a glass. The space-forming member 8 is preferably transparent or translucent but may be colored. Further, any opaque material may be used.

The opened portion 10 at the chromatography downstream end is opened without being covered with the liquid impermeable sheet 7, so that the liquid specimen volatilizes or evaporates when or after reaching the opened portion 10. Further, the liquid specimen exudes to the opened portion 10 and the liquid specimen only on the opened portion 10 of the development flow channel 2 reaches the same level or substantially the same level as the liquid specimen on the development flow channel 2 in the application space 9.

Example 1

Figure 14A:
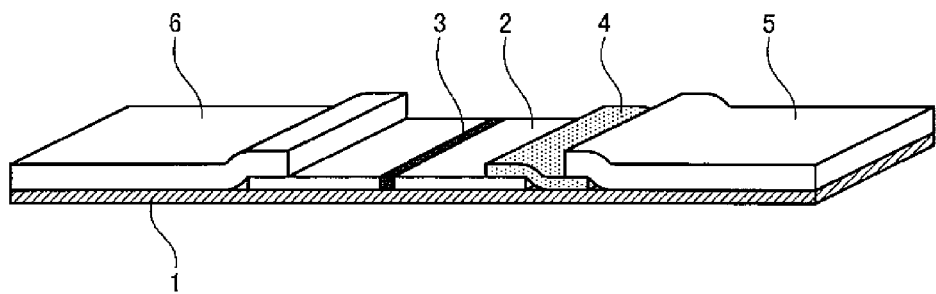
FIG. 14A is a perspective view of a conventional biosensor.
Figure 14B:
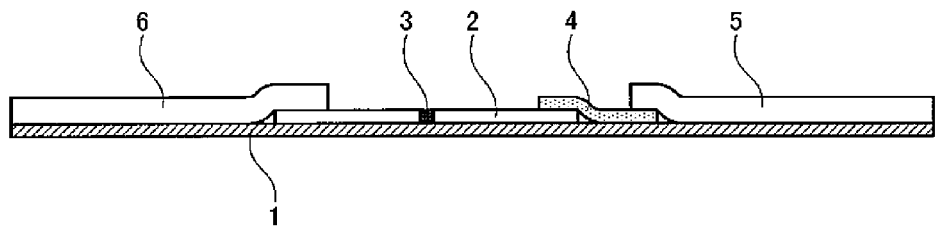
FIG. 14B is a vertical sectional view of the conventional biosensor.
Figure 14C:
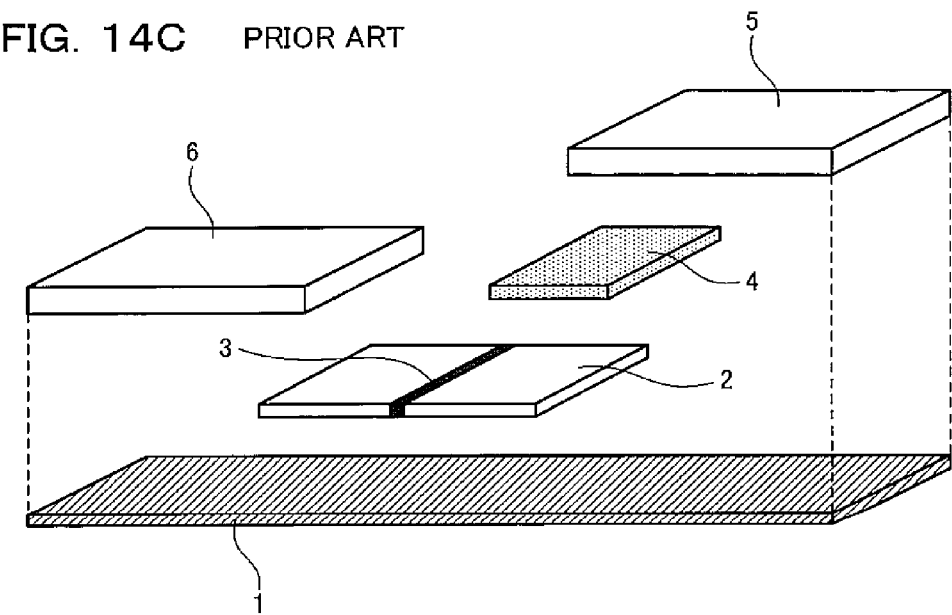
FIG. 14C is an exploded perspective view of the conventional biosensor.
Figure 15A:
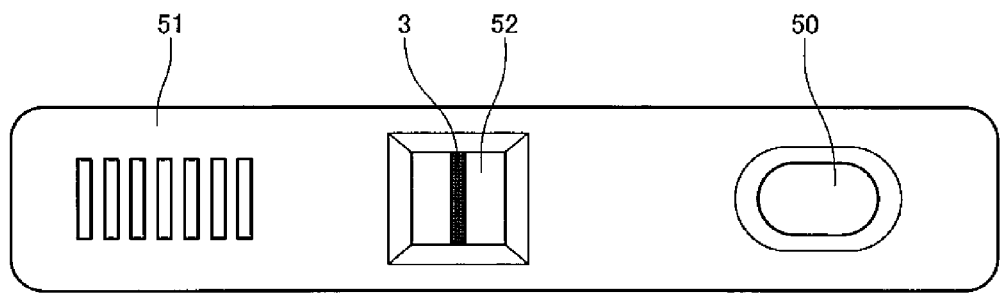
FIG. 15A is a plan view showing a final state where the conventional biosensor is housed in a casing.
Figure 15B:
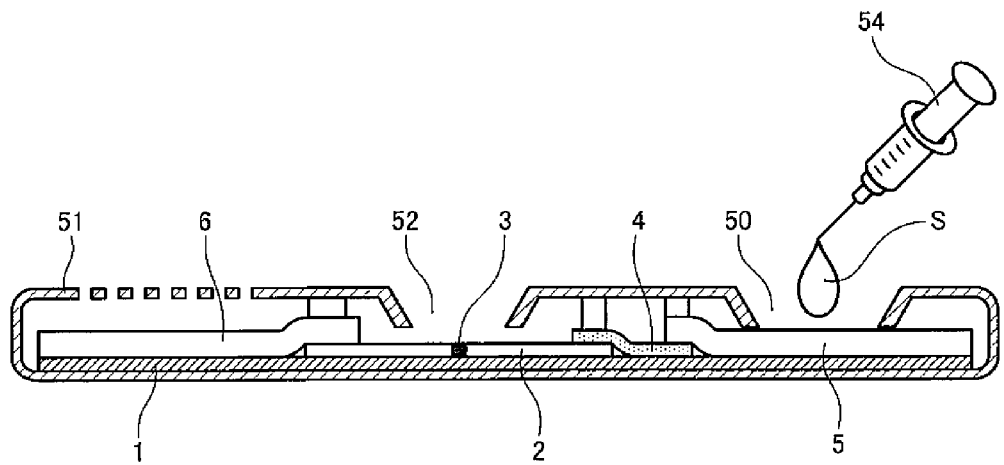
FIG. 15B is a side sectional view showing the final state where the conventional biosensor is housed in the casing.
Figure 16A:
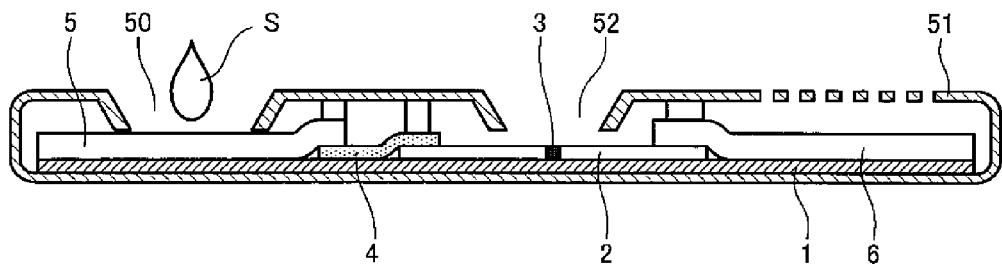
FIG. 16A is a sectional view showing the final state where the conventional biosensor is housed in the casing.
Figure 16B:
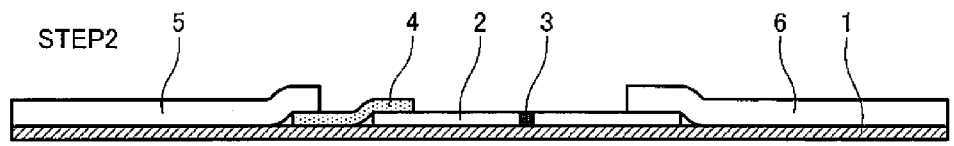
FIG. 16B is a sectional view of the biosensor showing a state of development of a liquid specimen on the conventional biosensor.
Figure 16C:
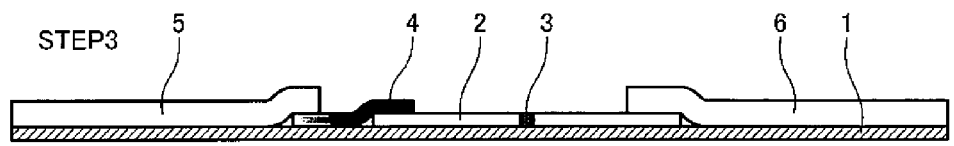
FIG. 16C is a sectional view of the biosensor showing the state of development of the liquid specimen on the conventional biosensor.
Figure 16D:
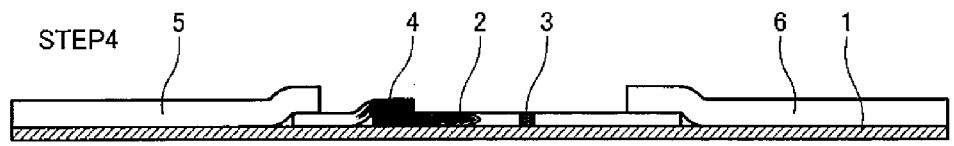
FIG. 16D is a sectional view of the biosensor showing the state of development of the liquid specimen on the conventional biosensor.
Figure 16E:
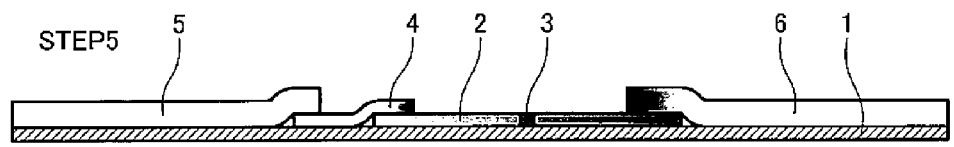
FIG. 16E is a sectional view of the biosensor showing the state of development of the liquid specimen on the conventional biosensor.
Figure 16F:
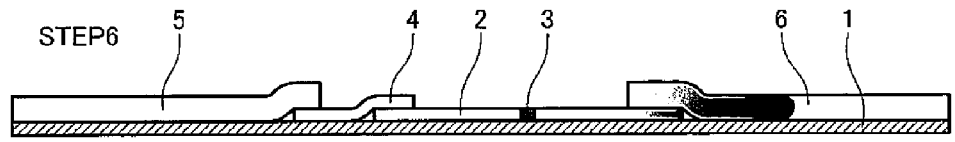
FIG. 16F is a sectional view of the biosensor showing the state of development of the liquid specimen on the conventional biosensor.
Figure 17A:
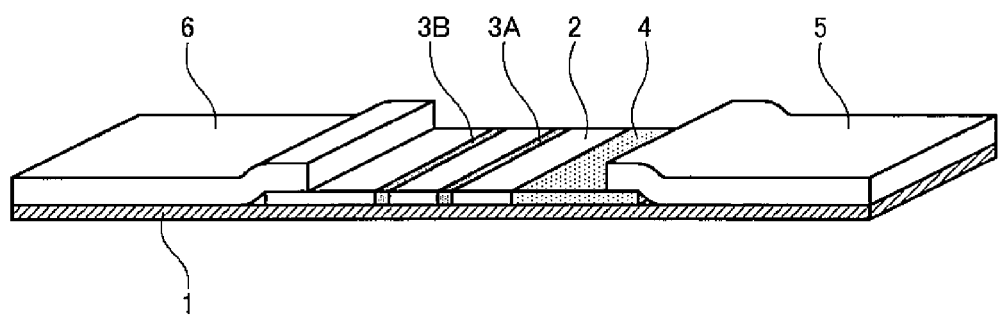
FIG. 17A is a perspective view of a biosensor of a comparative example.
Figure 17B:
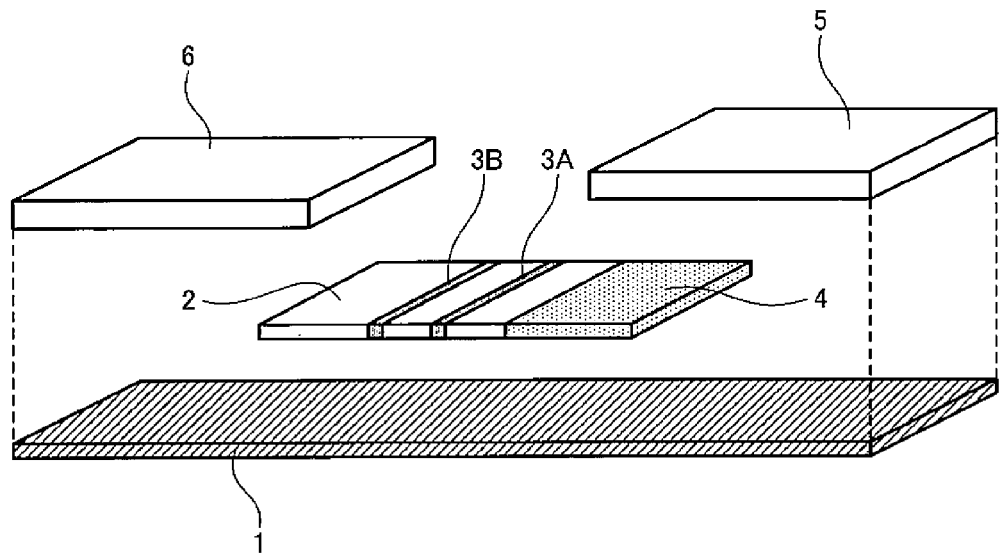
FIG. 17B is an exploded perspective view of the biosensor of the comparative example.

Quantification of CRP Using Plasma (a) Fabrication of Biosensor of Comparative Example First, a production method of a biosensor (immuno-chromatographic sensor) of a comparative example will be described. A structure of the biosensor of the comparative example will be simply described. FIG. 17A is a perspective view of the biosensor of the comparative example, and FIG. 17B is an exploded perspective view of the biosensor. As shown in FIGS. 17A and 173, the biosensor has substantially the same configuration as a conventional biosensor shown in FIGS. 14A to 14C, and includes, in a development flow channel 2, a first reagent-immobilized portion (also referred to as a first immobilized antibody line) 3A in which anti-CRP antibody A is immobilized, a second reagent-immobilized portion (also referred to as a second immobilized antibody line) 3B in which anti-CRP antibody B is immobilized, and a labeling-reagent retaining portion 4 retaining a complex (labeling-reagent) of anti-CRP antibody C and a gold colloid.

The biosensor was produced as follows:

A solution of anti-CRP antibody A was prepared. The concentration of the solution was adjusted by diluting the solution with a phosphate buffer. The antibody solution was applied on the nitrocellulose membrane by using a solution dispenser. Then, a solution of anti-CRP antibody B was similarly applied 4 mm downstream of the specimen application portion region 5. Thus, the first immobilized antibody line 3A and the second immobilized antibody line 3B serving as the reagent-immobilized portion 3 were obtained on the nitrocellulose membrane. After the nitrocellulose membrane was dried, the membrane was immersed into a Tris-HCl buffer solution containing 1% of skim milk and was gently swung for thirty minutes. After thirty minutes, the nitrocellulose membrane was moved into the bath of the Tris-HCl buffer solution and then was gently swung for ten minutes. After that, the nitrocellulose membrane was gently swung in another bath of the Tris-HCl buffer solution for ten minutes and then the membrane was cleaned. Next, the nitrocellulose membrane was immersed into a Tris-HCl buffer solution containing 0.050 of sucrose monolaurate and was gently swung for ten minutes. After that, the nitrocellulose membrane was removed from the bath and then was dried at room temperature. Thus, the development path 2 was obtained.

The gold colloid in the labeling-reagent was prepared by adding a solution containing 1% of trisodium citrate to a solution containing 0.01% of refluxing chloroauric acid at 100° C. After refluxing for 15 minutes, the solution was cooled at room temperature. Anti-CRP antibody C was added to the gold colloid solution having been prepared to pH 8.9 by 0.2 M of a potassium carbonate solution, and then the solution was stirred for several minutes. After that, a solution containing 10% of BSA (bovine serum albumin) of pH 8.9 was added to the solution and stirred such that the final amount of the BSA solution was 1%. The antibody-gold colloid complex (labeling-reagent) was prepared thus. The labeling-antibody solution was centrifugally separated at 4° C. and 20000 G for 50 minutes, so that the labeling-antibody was isolated. The labeling-antibody was suspended in a cleaning buffer solution (1% BSA 5% sucrose-phosphoric acid buffer solution) and then was subjected to the centrifugal separation, so that the labeling-antibody was cleaned and isolated. The labeling-antibody was suspended by a cleaning buffer solution and was filtered by a 0.8 μm filter. After that, the labeling-antibody was prepared to have an absorbance of 150 at 520 nm and was stored at 4° C. The labeling-antibody solution was set in a solution dispenser. The reaction reagent (labeling-reagent) was applied on a point separated from the first immobilized antibody line 3A and the second immobilized antibody line 3B on the dried membrane where the immobilized anti-CRP antibody A and the immobilized anti-CRP antibody B were applied so that the labeling-reagent retaining portion 4, the first immobilized antibody line 3A, and the second immobilized antibody line 3B were sequentially arranged in a liquid specimen application starting direction. After that, the nitrocellulose membrane was subjected to vacuum freeze-drying. Thus, the development flow channel 2 was obtained that included the labeling-reagent retaining portion 4 and the reagent-immobilized portion 3 (the first immobilized antibody line 3A and the second immobilized antibody line 3B).

Next, the development flow channel 2 containing the prepared reaction reagent (labeling-reagent) was bonded on a substrate 1 made of white PET with a thickness of 0.5 mm. The specimen application portion region 5 was bonded on a development upstream side of the labeling-reagent retaining portion 4 and the water absorbing portion 6 was bonded on a development downstream side of a rear end (downstream end) of the development flow channel so that the specimen application portion region 5 and the water absorbing portion 6 can be connected to the development flow channel 2 or the labeling-reagent retaining portion 4 by a capillary flow. After that, the substrate was cut to a width of 2.0 mm with laser. The biosensor as an immuno-chromatographic sensor having a conventional structure was produced thus.

(b) Fabrication of Biosensor of the Present Invention

Figure 4A:
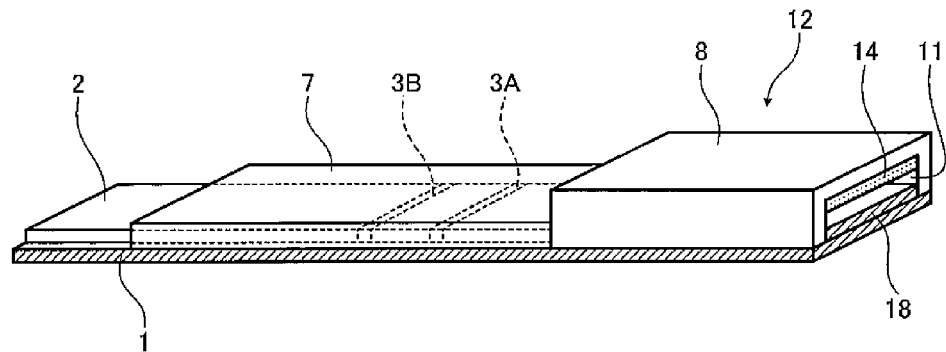
FIG. 4A is a perspective view of a biosensor according to another variant of the first embodiment.
Figure 4B:
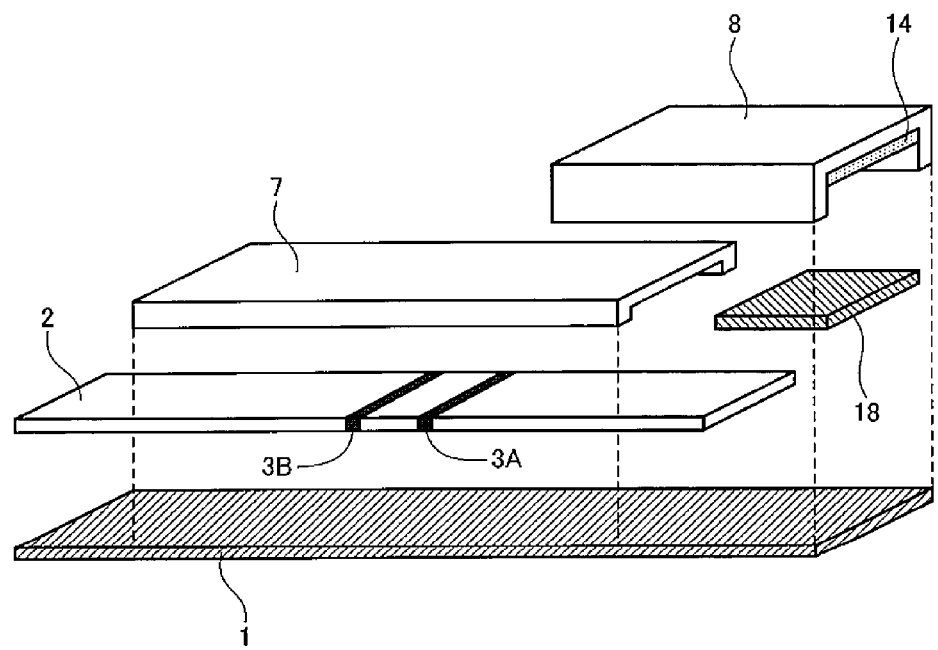
FIG. 4B is an exploded perspective view of the biosensor.

A production method of a biosensor (immuno-chromatographic sensor) of the present invention will be described. FIG. 4A is a perspective view of a biosensor according to another embodiment of the present invention, and FIG. 4B is an exploded perspective view of the biosensor. As shown in FIGS. 4A, 4B, and 1A to 1C, the biosensor has substantially the same configuration as the biosensor shown in FIGS. 1A to 1C, and includes, on a development flow channel 2 made of nitrocellulose membrane, a first reagent-immobilized portion (also referred to as a first immobilized antibody line) 3A in which anti-CRP antibody A was immobilized, a second reagent-immobilized portion (also referred to as a second immobilized antibody line) 3B in which anti-CRP antibody B was immobilized, and a reaction reagent 14 retaining a complex (labeling-reagent) of anti-CRP antibody C and a gold colloid.

The biosensor was produced as follows:

A solution of anti-CRP antibody A was prepared. The concentration of the solution was adjusted by diluting the solution with a phosphate buffer. The antibody solution was applied on the nitrocellulose membrane by using a solution dispenser. Then, a solution of anti-CRP antibody B was similarly applied 4 mm downstream of the specimen application portion 12. Thus, the first immobilized antibody line 3A and the second immobilized antibody line 3B serving as the reagent-immobilized portion 3 were obtained on the nitrocellulose membrane. After the nitrocellulose membrane was dried, the membrane was immersed into a Tris-HCl buffer solution containing 1% of skim milk and was gently swung for thirty minutes. After thirty minutes, the nitrocellulose membrane was moved into the bath of the Tris-HCl buffer solution and then was gently swung for ten minutes. After that, the nitrocellulose membrane was gently swung in another bath of the Tris-HCl buffer solution for ten minutes and then the membrane was cleaned. Next, the nitrocellulose membrane was immersed into a Tris-HCl buffer solution containing 0.05% of sucrose monolaurate and was gently swung for ten minutes. After that, the nitrocellulose membrane was removed from the bath and then was dried at room temperature. Thus, the development path 2 was obtained.

The gold colloid in the labeling-reagent 14 was prepared by adding a solution containing 1% of trisodium citrate to a solution containing 0.01% of refluxing chloroauric acid at 100° C. After refluxing for 15 minutes, the solution was cooled at room temperature. Anti-CRP antibody C was added to the gold colloid solution having been prepared to pH 8.9 by 0.2 M of a potassium carbonate solution, and then the solution was stirred for several minutes. After that, a solution containing 10% of BSA (bovine serum albumin) of pH 8.9 was added to the solution and stirred such that the final amount of the BSA solution was 1%. The antibody-gold colloid complex (labeling-antibody) was prepared thus. The labeling-antibody solution was centrifugally separated at 4° C. and 20000 G for 50 minutes, so that the labeling-antibody was isolated. The labeling-antibody was suspended in a cleaning buffer solution (1% BSA 5% sucrose-phosphoric acid buffer solution) and then was subjected to the centrifugal separation, so that the labeling-antibody was cleaned and isolated. The labeling-antibody was suspended by a cleaning buffer solution and was filtered by a 0.8 μm filter. After that, the labeling-antibody was prepared to have an absorbance of 50 at 520 nm and was stored at 4° C. After that, a space-forming member 8 fabricated by stacking transparent PET with a thickness of 100 μm was bonded, thereby forming a small application space (2.0 mm in width×7.0 mm in length×0.3 mm in height) 9. The labeling-antibody solution of 3 μl was applied to the application space 9 and dried, thereby obtaining the reaction reagent 14.

Next, the prepared development flow channel 2 was bonded on a substrate 1 made of white PET with a thickness of 0.5 mm. Transparent tape was bonded on a surface of the development flow channel 2 except chromatography development upstream and downstream sides of 3 mm each. After that, the substrate was cut to a width of 2.0 mm with laser. After the cutting, the space-forming member 8 retaining the reaction reagent 14 was bonded on a starting end (chromatography upstream side) where the transparent tape was not bonded, thereby forming the application space 9. The biosensor as an immuno-chromatographic sensor of the present invention was produced thus.

(c) Preparation of a Liquid Specimen

Plasma was separated from human blood to which heparin had been added as an anticoagulant, and a CRP solution with a known concentration was added to the plasma, so that plasma with CRP concentrations of 0.1 mg/dl and 1 mg/dl was prepared.

(d) Measurement of the Degree of Coloring on the Biosensor

Figure 5A:
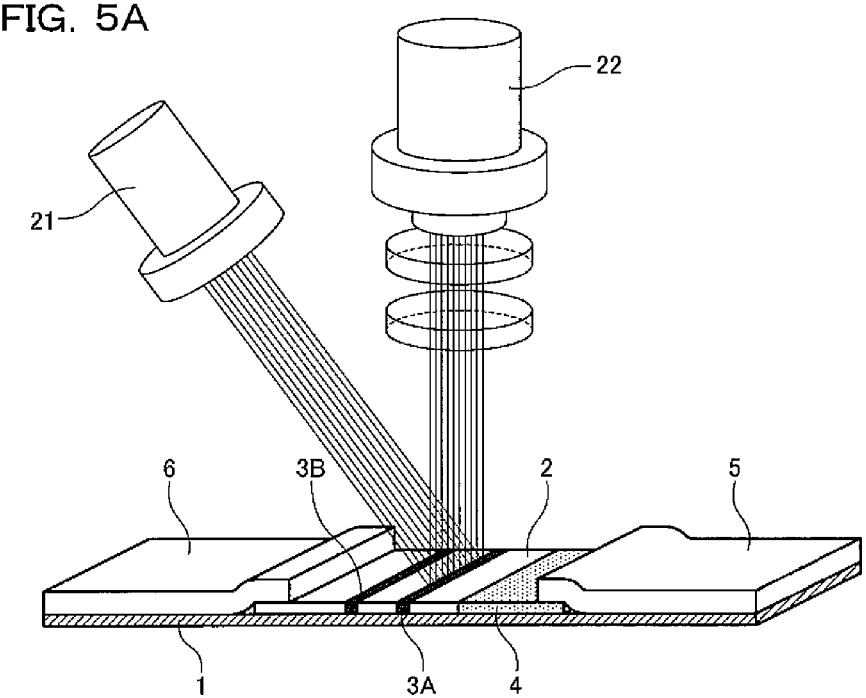
FIG. 5A is a schematic perspective view showing a state of measurement by a biosensor of a comparative example.
Figure 5B:
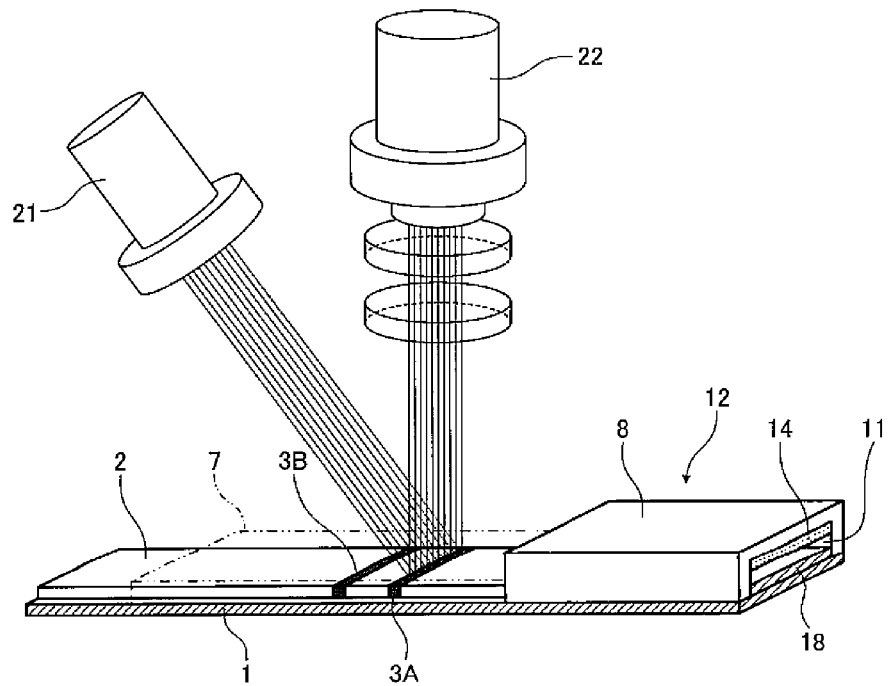
FIG. 5B is a schematic perspective view showing a state of measurement by a biosensor of this embodiment.
Figure 6A:
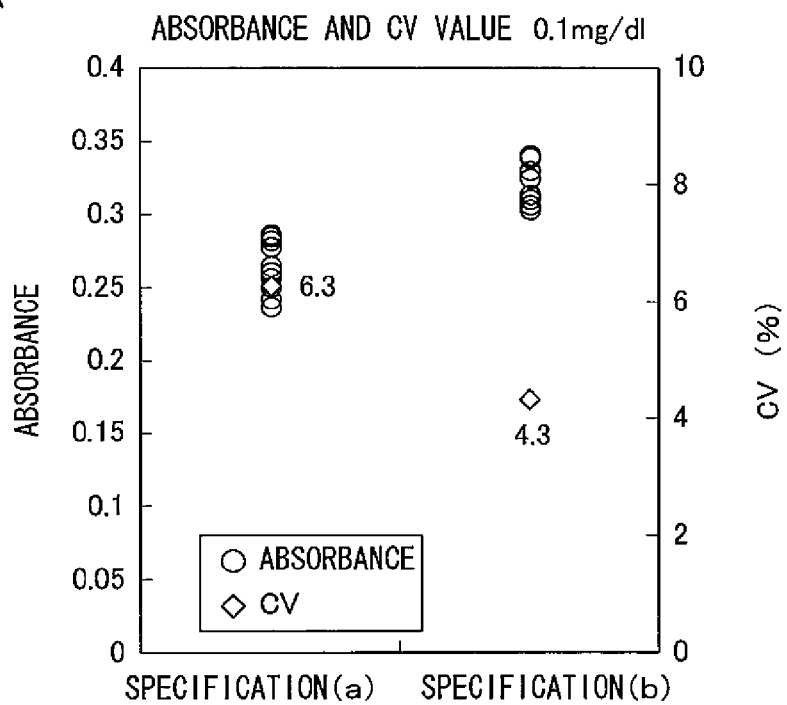
FIG. 6A shows absorbance distribution and a CV value as measurement results in Example 1 of the first embodiment of the present invention.
Figure 6B:
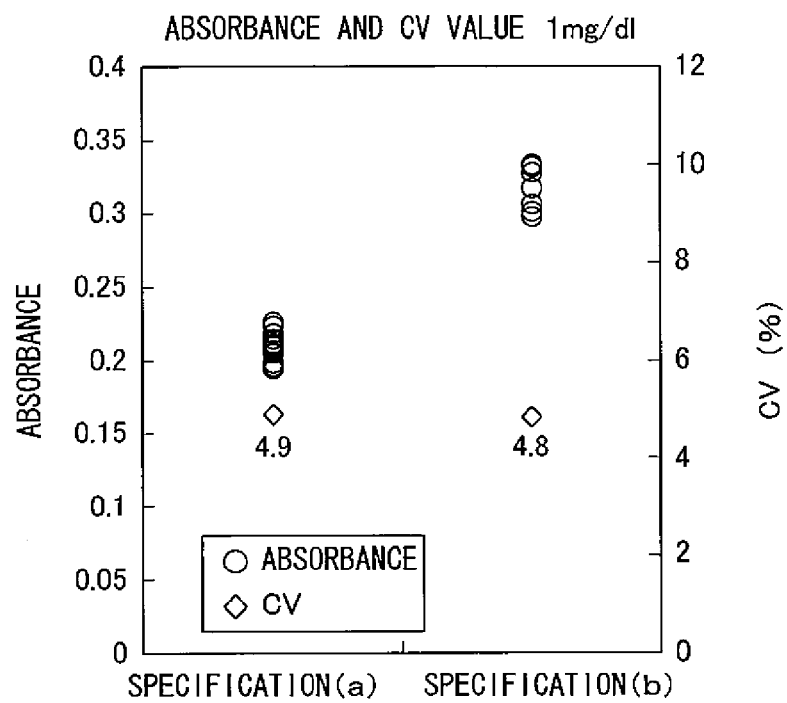
FIG. 6B shows absorbance distribution and a CV value as measurement results in Example 1 of the first embodiment of the present invention.

To the specimen application portions 5 and 12 of the biosensor fabricated in the fabricating steps (a) and (b), the plasma containing CRP prepared in the step (c) was applied. The liquid specimen was developed in the chromatography downstream direction and underwent an antigen-antibody reaction. The coloring states of the reagent-immobilized portions 3A and 3B were measured five minutes after the application of the liquid specimen to the biosensor fabricated in the steps (a) and (b). FIG. 5A is a schematic perspective view showing a state of measurement by a biosensor of a comparative example, and FIG. 5B is a schematic perspective view showing a state of measurement by the biosensor of this embodiment. In FIGS. 5A and 5B, reference numeral 21 denotes a light emitter including a semiconductor laser light source of 635 nm, and reference numeral 22 denotes a light receiver including a light receiving device (photodiode) that receives light reflected and scattered from the biosensor. In this configuration, the biosensor was scanned, and the amounts of binding of the labeling-antibody in the first reagent-immobilized portion 3A and the second reagent-immobilized portion 3B were obtained by calculating light reflected and scattered from the development flow channel 2, and an absorbance was obtained as a result. FIGS. 6A and 6B show measurement results when simultaneous reproducibility was measured of 10 biosensors (N=10) (conventional biosensors (specification (a)) fabricated in the steps (a) and (b) and the biosensor (specification (b)) according to the embodiment of the present invention.

FIGS. 6A and 6B show measurement results of absorbances of the first reagent-immobilized portion 3A and the second reagent-immobilized portion 3B. The first reagent-immobilized portion 3A is used for quantitative calculation at a CRP concentration of 0.1 mg/dl, and the second reagent-immobilized portion 3B is used for quantitative calculation at a CRP concentration of 1 mg/dl. Thus, an absorbance and a CV value of the first reagent-immobilized portion 3A are indicated at 0.1 mg/dl, and an absorbance and a CV value of the second reagent-immobilized portion 3B are indicated at 1 mg/dl. The CV value refers to standard deviation/average value×100.

As shown in FIGS. 6A and 6B, at either concentration, a lower absorbance was obtained in the specification (a) than the specification (b). As described in the problems of the present invention, the low absorbance was obtained in the conventional biosensor because the labeling-reagent carried on the development flow channel 2 was not completely dissolved, and the CRP as an analyte in the applied liquid specimen did not sufficiently react with the labeling-reagent. The high absorbance was obtained in the specification (b), that is, in the biosensor of the present invention because the above two points were solved. Specifically, the labeling-reagent was completely dissolved, the analyte, the CRP, and the labeling-reagent sufficiently reacted with each other, and the reacted liquid specimen was able to be sufficiently developed in the development flow channel 2.

The CV value was further compared. Then, it was found that there was no significant difference in CV value between the specifications, and using plasma with low viscosity and high developability as a specimen did not cause large variations in the development. From the results, it was supposed that the difference in absorbance between the two specifications was caused by an area and a carrier retaining the labeling-reagent, and the present invention increases sensitivity and allows measurement with high sensitivity. In the biosensor in Example 1 of the present invention, liquid permeable components can be reduced to significantly reduce the amount of specimen.

Example 2

Quantification of CRP in Blood Using Whole Blood (a) Fabrication of Biosensor of Comparative Example A biosensor was produced including a first reagent-immobilized portion (also referred to as a first immobilized antibody line) 3A in which anti-CRP antibody A was immobilized, a second reagent-immobilized portion (also referred to as a second immobilized antibody line) 3B in which anti-CRP antibody B was immobilized, and a labeling-reagent retaining portion 4 retaining a complex (labeling-reagent) of anti-CRP antibody C and a gold colloid. FIG. 17A is a perspective view of the biosensor of the comparative example, and FIG. 17B is an exploded perspective view of the biosensor.

The immuno-chromatographic sensor was produced as follows:

A solution of anti-CRP antibody A was prepared. The concentration of the solution was adjusted by diluting the solution with a phosphate buffer. The antibody solution was applied on the nitrocellulose membrane by using a solution dispenser. Then, a solution of anti-CRP antibody B was similarly applied 4 mm downstream of the specimen application portion. Thus, the first immobilized antibody line 3A and the second immobilized antibody line 3B serving as the reagent-immobilized portion 3 were obtained on the nitrocellulose membrane. After the nitrocellulose membrane was dried, the membrane was immersed into a Tris-HCl buffer solution containing 10 of skim milk and was gently swung for thirty minutes. After thirty minutes, the nitrocellulose membrane was moved into the bath of the Tris-HCl buffer solution and then was gently swung for ten minutes. After that, the nitrocellulose membrane was gently swung in another bath of the Tris-HCl buffer solution for ten minutes and then the membrane was cleaned. Next, the nitrocellulose membrane was immersed into a Tris-HCl buffer solution containing 0.05% of sucrose monolaurate and was gently swung for ten minutes. After that, the membrane was removed from the bath and then was dried at room temperature. Thus, the development path 2 was obtained.

The gold colloid in the labeling-reagent was prepared by adding a solution containing 10 of trisodium citrate to a solution containing 0.01% of refluxing chloroauric acid at 100° C. After refluxing for 15 minutes, the solution was cooled at room temperature. Anti-CRP antibody C was added to the gold colloid solution having been prepared to pH 8.9 by 0.2 M of a potassium carbonate solution, and then the solution was stirred for several minutes. After that, a solution containing 10% of BSA (bovine serum albumin) of pH 8.9 was added to the solution and stirred such that the final amount of the BSA solution was 1%. The antibody-gold colloid complex (labeling-antibody) was prepared thus. The labeling-antibody solution was centrifugally separated at 4° C. and 20000 G for 50 minutes, so that the labeling-antibody was isolated. The labeling-antibody was suspended in a cleaning buffer solution (1% BSA 5% sucrose-phosphoric acid buffer solution) and then was subjected to the centrifugal separation, so that the labeling-antibody was cleaned and isolated. The labeling-antibody was suspended by a cleaning buffer solution and was filtered by a 0.8 filter. After that, the labeling-antibody was prepared to have an absorbance of 150 at 520 nm and was stored at 4° C. The labeling-antibody solution was set in a solution dispenser. The reaction reagent (labeling-reagent) was applied on a point separated from the first immobilized antibody line 3A and the second immobilized antibody line 3B on the dried membrane where the immobilized anti-CRP antibody A and the immobilized anti-CRP antibody B were applied so that the labeling-reagent retaining portion 4, the first immobilized antibody line 3A, and the second immobilized antibody line 3B were sequentially arranged in a liquid specimen application starting direction. After that, the nitrocellulose membrane was subjected to vacuum freeze-drying. Thus, the development flow channel 2 was obtained that included the labeling-reagent retaining portion 4 and the reagent-immobilized portion 3 (the first immobilized antibody line 3A and the second immobilized antibody line 3B).

Next, the reaction layer carrier containing the prepared labeling-reagent was bonded on a substrate 1 made of white PET with a thickness of 0.5 mm, and transparent tape was bonded from the labeling-reagent retaining portion 4 to the rear end. After that, the substrate was cut to a width of 2.0 mm with laser. After the cutting, a space-forming member 8 fabricated by stacking transparent PET with a thickness of 100 μm was bonded on the starting end where the transparent tape was not bonded, thereby forming a small application space (2.0 mm in width×7.0 mm in length×0.3 mm in height) 9.

The space-forming member 8 was immediately frozen by liquid nitrogen after dropping of a solution containing 10% of potassium chloride, and then the space-forming member 8 was subjected to freeze-drying. Thus, a biosensor including the space-forming member 8 was fabricated in which a cell component shrinkage agent containing dried potassium chloride was retained. The immuno-chromatographic sensor of the comparative example was produced thus. Specifically, the biosensor of the comparative example includes the same space-forming member 8 as shown in FIGS. 4A and 4B, although not shown in FIGS. 17A and 17B. However, only a cell component shrinkage agent is retained in the space-forming member 8. The labeling-reagent retaining portion 4 is provided in an upstream region of the reaction layer carrier (development flow channel 2).

b) Fabrication of Immuno-Chromatographic Sensor of the Present Invention

A biosensor of the present invention was produced including, on a nitrocellulose membrane, a first reagent-immobilized portion (also referred to as a first immobilized antibody line) 3A, a second reagent-immobilized portion (also referred to as a second immobilized antibody line) 3B in which anti-CRP antibody B was immobilized, and a reaction reagent 14 retaining a complex (labeling-reagent) of anti-CRP antibody C and a gold colloid and a cell component shrinkage agent. FIG. 4A is a perspective view of the biosensor and FIG. 4B is an exploded perspective view.

The biosensor was produced as follows:

A solution of anti-CRP antibody A was prepared. The concentration of the solution was adjusted by diluting the solution with a phosphate buffer. The antibody solution was applied on the nitrocellulose membrane by using a solution dispenser. Then, a solution of anti-CRP antibody B was similarly applied 4 mm downstream of the specimen application portion 12. Thus, the first immobilized antibody line 3A and the second immobilized antibody line 3B in which anti-CRP antibody B was immobilized serving as the reagent-immobilized portion 3 were obtained on the nitrocellulose membrane. After the nitrocellulose membrane was dried, the membrane was immersed into a Tris-HCl buffer solution containing 1% of skim milk and was gently swung for thirty minutes. After thirty minutes, the nitrocellulose membrane was moved into the bath of the Tris-HCl buffer solution and then was gently swung for ten minutes. After that, the nitrocellulose membrane was gently swung in another bath of the Tris-HCl buffer solution for ten minutes and then the membrane was cleaned. Next, the nitrocellulose membrane was immersed into a Tris-HCl buffer solution containing 0.05% of sucrose monolaurate and was gently swung for ten minutes. After that, the membrane was removed from the bath and then was dried at room temperature. Thus, the development path 2 was obtained.

The gold colloid in the labeling-reagent was prepared by adding a solution containing 1% of trisodium citrate to a solution containing 0.01% of refluxing chloroauric acid at 100° C. After refluxing for 15 minutes, the solution was cooled at room temperature. Anti-CRP antibody C was added to the gold colloid solution having been prepared to pH 8.9 by 0.2 M of a potassium carbonate solution, and then the solution was stirred for several minutes. After that, a solution containing 10% of BSA (bovine serum albumin) of pH 8.9 was added to the solution and stirred such that the final amount of the BSA solution was 1%. The antibody-gold colloid complex (labeling-reagent) was prepared thus. The labeling-antibody solution was centrifugally separated at 4° C. and 20000 G for 50 minutes, so that the labeling-antibody was isolated. The labeling-antibody was suspended in a cleaning buffer solution (1% BSA 5% sucrose-phosphoric acid buffer solution) and then was subjected to the centrifugal separation, so that the labeling-antibody was cleaned and isolated. The labeling-antibody was suspended by a cleaning buffer solution and was filtered by a 0.8 μm filter. After that, the labeling-antibody was prepared to have an absorbance of 50 at 520 nm. Further, potassium chloride was added to the labeling-antibody solution such that the final concentration was 10%. A labeling-antibody-cell component shrinkage agent mixed solution was prepared and stored at 4° C. After that, a space-forming member 8 fabricated by stacking transparent PET with a thickness of 100 μm was bonded, thereby forming an application space (2.0 mm in width×7.0 mm in length×0.3 mm in height) 9. The labeling-antibody-cell component shrinkage agent mixed solution of 3 μl was applied to the application space 9 and dried, thereby obtaining the reaction reagent 14.

Next, the prepared development flow channel was bonded on a substrate 1 made of white PET with a thickness of 0.5 mm. Transparent tape was bonded on a surface of the development flow channel 2 except chromatography development upstream and downstream sides of 3 mm each. After that, the substrate was cut to a width of 2.0 mm with laser. After the cutting, the space-forming member 8 retaining the reaction reagent 14 was bonded on a starting end (chromatography upstream side) where the transparent tape was not bonded, thereby forming the application space 9. The biosensor of the present invention was produced thus.

c) Preparation of a Liquid Specimen

A CRP solution with a known concentration was added to human blood to which heparin had been added as an anticoagulant, so that blood (whole blood) with CRP concentrations of 0.1 mg/dl and 1 mg/dl was prepared.

d) Measurement of the Degree of Coloring on the Biosensor

Figure 7A:
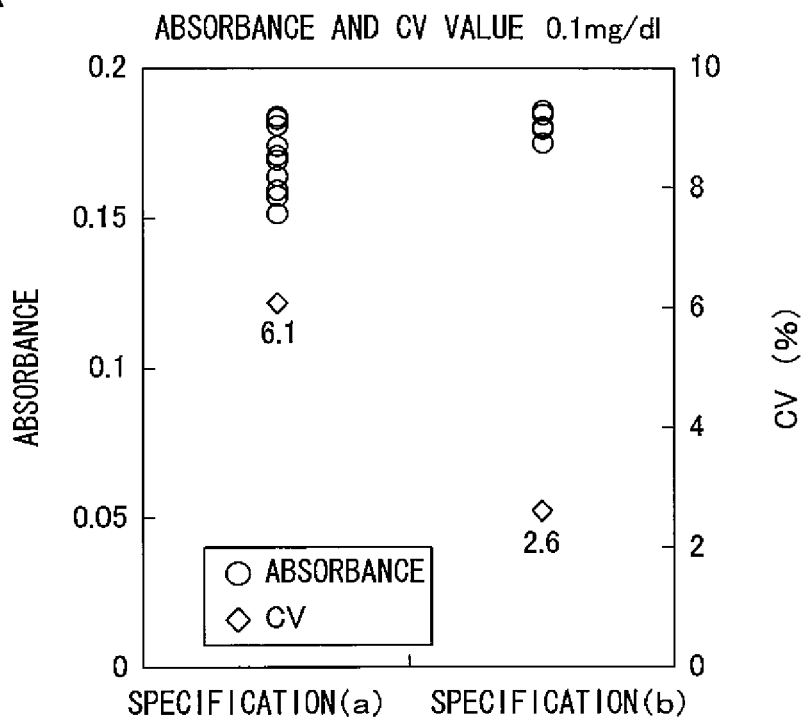
FIG. 7A shows absorbance distribution and a CV value as measurement results in Example 2 of the first embodiment of the present invention.
Figure 7B:
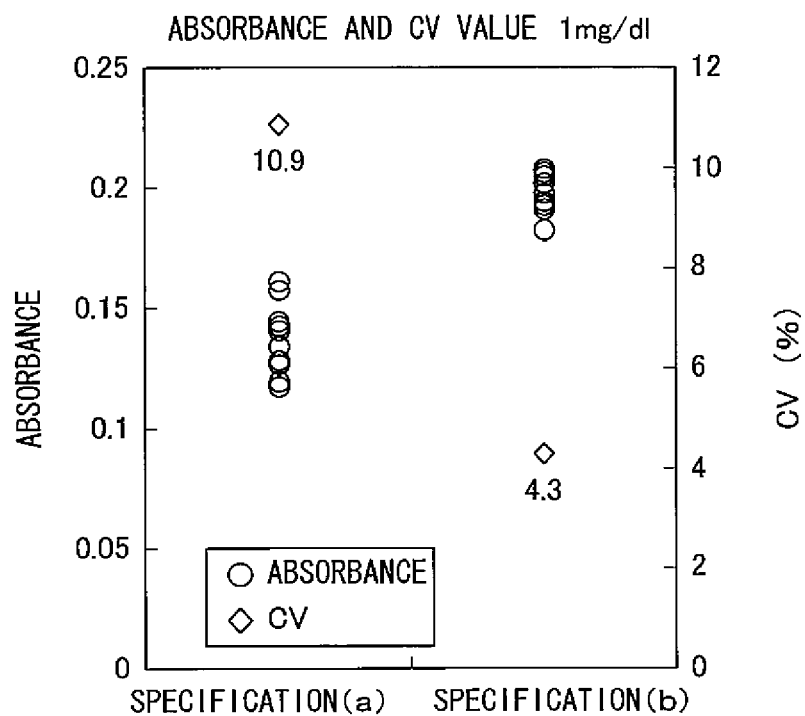
FIG. 7B shows absorbance distribution and a CV value as measurement results in Example 2 of the first embodiment of the present invention.

To the specimen application portions 5 and 12 of the biosensor produced in the fabricating steps (a) and (b), the whole blood containing CRP prepared in the step (c) was applied. The liquid specimen was developed in the chromatography downstream direction and underwent an antigen-antibody reaction. The coloring states of the reagent-immobilized portions 3A and 3B were measured five minutes after the application of the liquid specimen to the biosensor fabricated in the steps (a) and (b). FIG. 5A is a schematic perspective view showing the state of measurement by the conventional biosensor, and FIG. 5B is a schematic perspective view showing the state of measurement by the biosensor of this embodiment. In FIGS. 5A and 5B, reference numeral 21 denotes a light emitter including a semiconductor laser light source of 635 nm, and reference numeral 22 denotes a light receiver including a light receiving device (photodiode) that receives light reflected and scattered from the biosensor. In this configuration, the biosensor was scanned, and the amounts of binding of the labeling-antibody in the first reagent-immobilized portion 3A and the second reagent-immobilized portion 3B were obtained by calculating light reflected and scattered from the development flow channel 2, and an absorbance was obtained as a result. FIGS. 7A and 7B show measurement results when simultaneous reproducibility was measured of 10 biosensors (N=10) (conventional biosensors (specification (a)) fabricated in the steps (a) and (b) and the biosensor (specification (b)) according to the embodiment of the present invention.

FIGS. 7A and 7B show measurement results of absorbances of the first reagent-immobilized portion 3A and the second reagent-immobilized portion 3B. The first reagent-immobilized portion 3A is used for quantitative calculation at a CRP concentration of 0.1 mg/dl, and the second reagent-immobilized portion 3B is used for quantitative calculation at a CRP concentration of 1 mg/dl. Thus, an absorbance and a CV value of the first reagent-immobilized portion 3A are indicated at 0.1 mg/dl, and an absorbance and a CV value of the second reagent-immobilized portion 3B are indicated at 1 mg/dl.

As shown in FIGS. 7A and 7B, at either concentration, a lower absorbance was obtained in the specification (a) than the specification (b). As described in the problems of the present invention, the low absorbance was obtained in the conventional biosensor because the labeling-reagent carried on the development flow channel 2 was not completely dissolved, and the CRP as an analyte in the applied liquid specimen did not sufficiently react with the labeling-reagent. The high absorbance was obtained in the specification (b), that is, in the biosensor of the present invention because the above two points were solved. Specifically, the labeling-reagent was completely dissolved, the analyte, the CRP, and the labeling-reagent sufficiently reacted with each other, and the reacted liquid specimen was able to be sufficiently developed in the development flow channel 2.

The CV value was further compared. Then, the specification (b), that is, the biosensor of the present invention obtains a higher CV value. In this example, the solution is nonuniformly developed in the development flow channel 2 because the whole blood is developed. However, variations in absorbance of the specifications (b) are extremely small, and substantially the same results can be obtained as in Example 1 in which the plasma was developed. This is because the labeling-reagent, the cell component shrinkage agent, and the whole blood uniformly react with each other in the application space 9. The whole blood can simultaneously react with both of the reagents, so that more uniform reaction is performed, thereby improving developability of the solution.

As described above, from the results of Examples 1 and 2, it was confirmed that the present invention provides a biosensor as an immuno-chromatographic sensor that allows easy and quick measurement with precision, high accuracy, and high sensitivity.

In Examples 1 and 2, the biosensor is used in which the reagent-immobilized portions 3, 3A and 3B or the like are provided on the nitrocellulose membrane. The material of the development flow channel 2 is not limited to the nitrocellulose membrane and any porous material such as filter paper, nonwoven fabric, membrane, fabric, and glass fiber may be used as long as the material is wet with the liquid specimen and can form a passage for development of the liquid specimen. The passage may be formed of a hollow capillary, and such a hollow capillary may be made of a resin material or the like.

The gold colloid is taken as an example of a marker that forms the labeling-reagent, but coloring matters, fluorescent substances, phosphorescent substances, light emitting substances, redox substances, enzymes, nucleic acids, or endoplasmic reticulum may be used. Any material may be selected when necessary as long as the material changes between before and after the reaction. A reagent such as a modifier or a matrix may be contained depending on reaction systems.

Any antibodies may be used for the first reagent-immobilized portion 3A and the second reagent-immobilized portion 3B as long as a complex of the labeling-reagent and the analyte can be formed. Thus, epitopes and affinities for the analyte may be the same or different from each other. Alternatively, the two antibodies may have different affinities but have the same epitope.

The degree of coloring is read by detecting the development state of the liquid specimen by optical changes using the light emitter 21 and the light receiver 22. Alternatively, the degree of coloring may be read by any method such as reading electrical or electromagnetic changes or capturing an image.

The reagent using potassium chloride as a cell component shrinkage agent is described. The cell component shrinkage agent is a reagent to be provided when a liquid specimen contains a cell component. The cell component shrinkage agent is not required when a liquid specimen that does not contain a cell component is used. The cell component shrinkage agent may be inorganic compounds such as potassium chloride, sodium chloride, or sodium phosphate that shrink cells, amino acids such as glycine or glutamic acid, imino acids such as praline, saccharides such as glucose, sucrose, or trehalose, or sugar alcohol such as glucitol. A system including such a cell component shrinkage agent is particularly useful when whole blood is used as a liquid specimen. In this embodiment, the case is exemplified where the labeling-reagent or the mixed solution of the labeling-reagent and the cell component shrinkage agent is carried in the small space. Any other reagents may be solely carried or mixed and carried.

In the above-described embodiment, the reaction reagent 14 containing a tracer is retained on the back side of the upper surface of the space-forming member 8. The back side is spaced a predetermined distance apart from and faces the upper surface of the substrate 1 on which the development flow channel 2 is provided. In this case, the tracer (labeling-reagent) can be introduced into the development flow channel 2 in a state where the tracer is more uniformly dissolved into the liquid specimen than the case where the tracer is provided on the upper surface (bottom surface of the application space) of the substrate 1. Thus, measurement results with higher precision, higher accuracy, and higher sensitivity can be obtained. Specifically, when the reaction reagent 14 is provided on the bottom surface of the specimen application portion 12, that is, the upper surface of the substrate 1, the reaction reagent 14 and the chromatography upstream end region of the development flow channel 2 are brought into contact with or extremely close to each other. In this case, a nonuniform liquid specimen immediately after the labeling-reagent is dissolved into the liquid specimen may be introduced into the development flow channel 2 to reduce accuracy or sensitivity. The above-described configuration can prevent such defects.

The reaction reagent 14 containing a tracer is not limited to the above-described configuration. The reaction reagent 14 may be provided on an inner side of the side surface or the like of the space-forming member 8. Also in this case, it is desirable that the reaction reagent 14 is not in contact with the development flow channel 2 but is spaced apart from the development flow channel 2.

The method is exemplified in which a certain amount of labeling-reagent is applied and then dried in the application space. The reagent may be placed in any position on the back side of the upper surface or the side surface extending upward from the bottom surface such that the reagent is placed over the entire back side of the upper surface or the entire side surface extending upward from the bottom surface, or the reagent is placed on a part of either surface. Any unit may be used such that the reagent is retained in a state where the reagent can be dissolved into the liquid specimen applied to the application space by spraying rather than applying.

The liquid specimens to be measured include, for example, water, solutions, body fluids such as urine, plasma, serum, and saliva, and solutions in which a solid, powder, or gas is dissolved. The liquid specimens are used for, for example, a blood test, a urinalysis, a water examination, a fecal examination, a soil analysis, and a food analysis. Further, in the examples, a C-reactive protein (CRP) is exemplified as the test substance, but the test substances may include antibodies, immunogloblins, hormones, proteins such as enzymes and peptides, protein derivatives, bacteria, viruses, funguses, mycoplasmas, parasites, infectious substances including products and components thereof, therapeutic agents, drugs such as drugs of abuse, and tumor markers. Specifically, the test substances may include human chorionic gonadotropin (hCG), luteinizing hormones (LH), thyroid-stimulating hormones, follicle stimulating hormones, parathyroid stimulating hormones, adrenocorticotropic hormones, estradiols, prostate specific antigens, hepatitis, myoglobins, CRPs, cardiac troponins, HbA1cs, and albumins. Further, the present invention can be implemented for environmental analyses such as water examinations and soil analyses, food analyses, and so on. The present invention makes it possible to easily and quickly conduct measurement with high sensitivity and high performance and allow measurement anywhere at anytime by anyone. Thus, the present invention is usable as an analyzing device for POCT.

A second embodiment of a biosensor according to the present invention will be specifically described below with reference to the accompanying drawings. The following embodiment is merely exemplary and the present invention is not always limited to the following embodiment.

Figure 8:
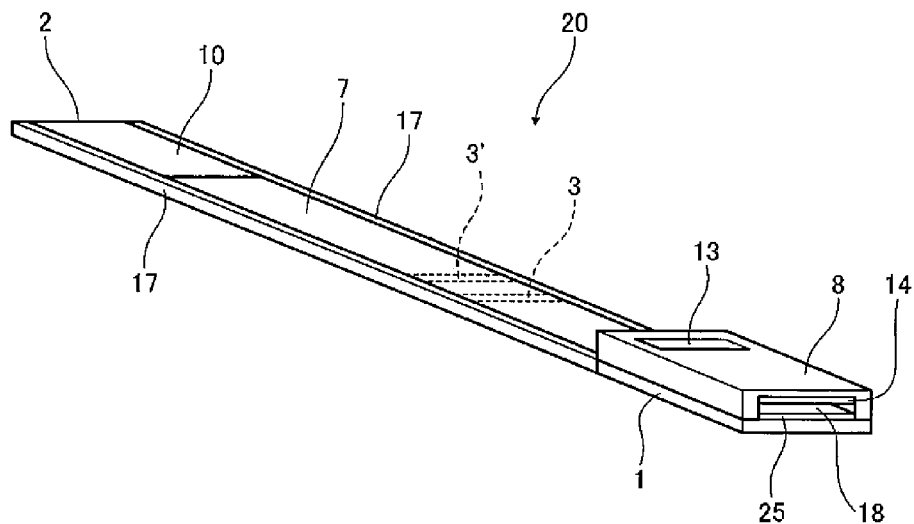
FIG. 8 is a perspective view showing a configuration of a biosensor according to a second embodiment of the present invention.
Figure 9:
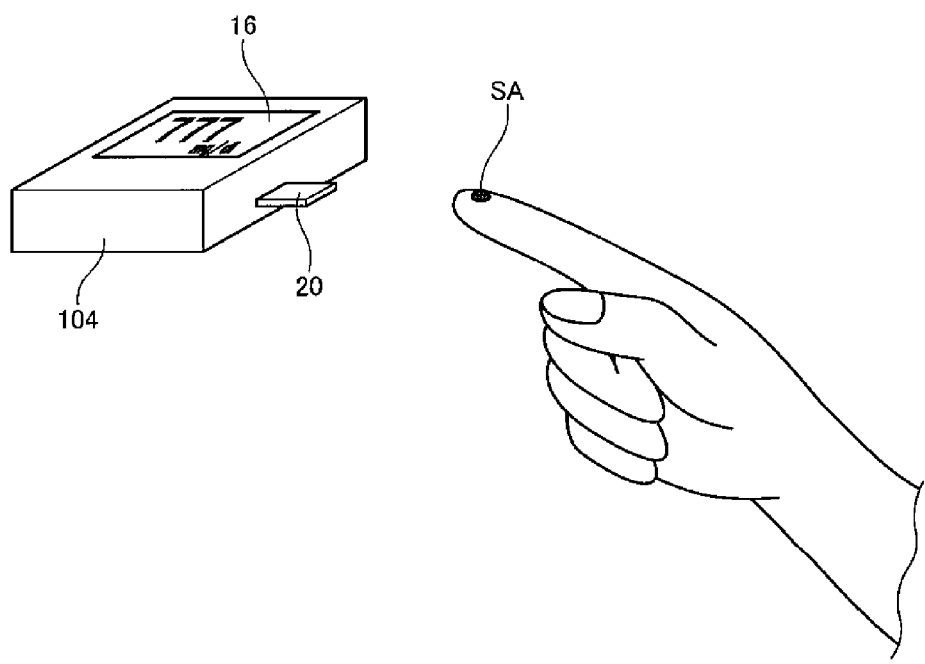
FIG. 9 is a schematic perspective view showing an analysis state using the biosensor and an analyzing device.
Figure 10A:
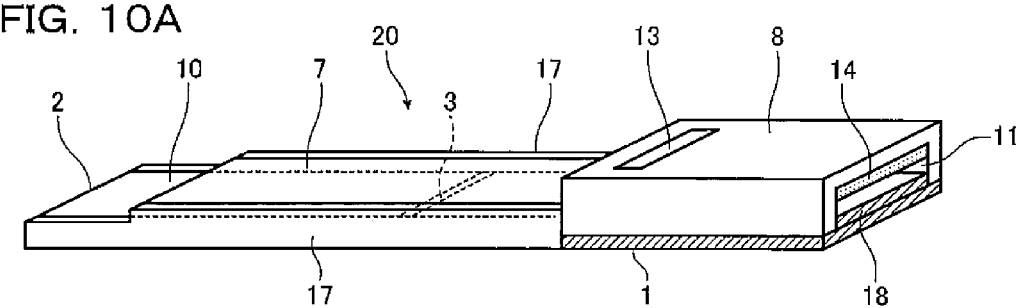
FIG. 10A is a perspective view of the biosensor.
Figure 10B:
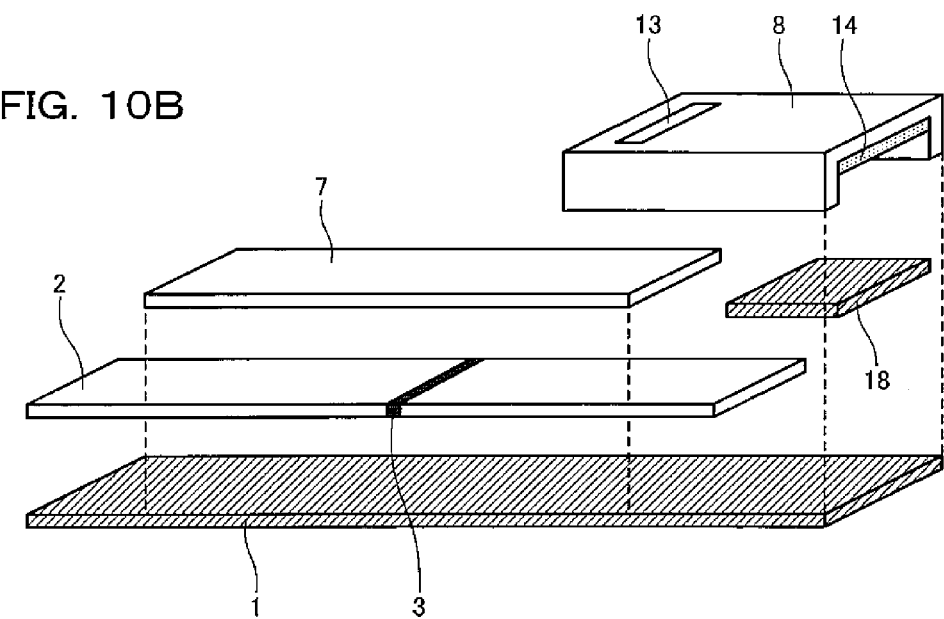
FIG. 10B is an exploded perspective view of the biosensor.
Figure 10C:
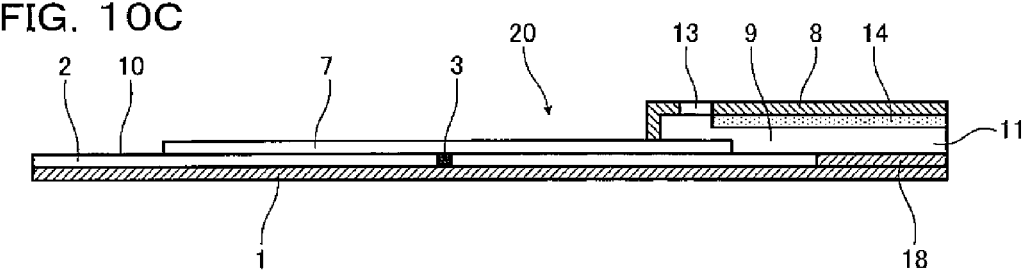
FIG. 10C is a sectional view when the biosensor is cut in a longitudinal direction.
Figure 10D:
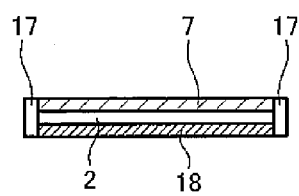
FIG. 10D is a sectional view when the biosensor is cut in a width direction.

FIG. 8 is a perspective view showing a biosensor according to this embodiment, and FIG. 9 is a schematic perspective view showing an analysis state using the biosensor and an analyzing device. FIGS. 10A, 10B, 10C and 10D show a configuration of the biosensor shown in FIG. 8, FIG. 10A is a perspective view of the biosensor, FIG. 10B is an exploded perspective view of the biosensor, FIG. 10C is a vertical sectional view of the biosensor, and FIG. 10D is a cross sectional view of the biosensor.

As shown in FIGS. 10A to 10D, a biosensor (test piece) 20 includes an application space (capillary chamber) 9 that sips and retains a blood sample S as an applied liquid specimen with a capillary force, a development flow channel 2 in which the blood sample S and a reaction reagent that can specifically react with an analyte in the blood sample S are developed, and a substrate 1 as a support that forms a bottom surface of the application space 9 and supports the development flow channel 2, and measures presence and absence or a concentration of the analyte in the blood sample S using chromatography. The application space 9 is formed by placing a space-forming member 8 on one end (upstream end in a chromatography development direction described later) of the substrate 1 so that the space-forming member 8 surrounds the application space 9 as a small space from above and both sides, and joining lower surfaces of the both sides of the space-forming member 8. An upstream portion of the development flow channel 2 protrudes into the application space 9 through a hole portion formed in one end, and an opening 11 for applying the blood sample is formed in the other end of the application space 9. Further, an air hole 13 for boosting the capillary force is opened in an upper surface of one end of the space-forming member 8 for forming the application space 9.

In the application space 9, a reaction reagent 14 containing a labeling-reagent is retained in a state where the reaction reagent 14 can be dissolved into the blood sample applied to the application space 9 and mixed and reacted with the blood sample. The labeling-reagent includes a ligand portion and a detectable labeling portion bound to the ligand portion. The reaction reagent 14 contains the labeling-reagent and also contains a blood cell component shrinkage agent that reacts with a blood cell component in a blood sample and shrinks the blood cell component.

The reaction reagent 14 containing the labeling-reagent is carried in a position not on an extension of the development flow channel along a thickness direction of the development flow channel 2 in the application space 9 without contact with the development flow channel 2 or the substrate 1. In this embodiment, the reaction reagent 14 is retained on the back side of the upper surface of the space-forming member 8. The back side is spaced a predetermined distance apart from and faces the upper surface of the substrate 1 on which the development flow channel 2 is provided via the application space 9 along a thickness direction thereof.

In a part of the development flow channel 2, a reagent-immobilized portion 3 in which a specific protein is immobilized is provided. The reagent-immobilized portion 3 is also used as a measurement region. A liquid impermeable sheet 7 made of a liquid impermeable material covers a surface of the development flow channel 2 from a chromatography upstream region outside the application space 9 to a chromatography downstream region including at least the reagent-immobilized portion 3. The liquid impermeable sheet 7 does not cover an upstream end portion (upstream end region in a chromatography development direction) of the development path 2 entering the application space 9, and an opened portion 10 in a downstream end region (also referred to as chromatography downstream end) in a chromatography development direction. The chromatography upstream region of the development flow channel 2 enters the application space 9 from the space-forming member 8. As shown in FIG. 10C, the application space 9 is a space corresponding to a chromatography upstream end for sipping a certain amount of blood sample by capillarity, and a tip (the other end) of the application space 9 is an opening 11 for sipping a blood sample into the biosensor.

As shown in FIGS. 10B and 10C, the substrate 1 and the application space 9 are joined so that ends of the substrate 1 and the application space 9 (ends in the chromatography upstream region) are aligned, thereby forming the opening 11. The upstream end of the development flow channel 2, that is, the end of the chromatography upstream region of the development flow channel 2 is provided only to a position on a deeper side in a suction direction than the opening 11 for sipping a blood sample in the application space 9, that is, a downstream position in the chromatography development direction. The development flow channel 2 is not provided in a region between the upstream end of the development flow channel 2 and the opening 11.

If nothing is provided in the region where the development flow channel 2 is not provided on the substrate 1 in the application space 9, that is, the region between the upstream end of the development flow channel 2 entering the application space 9 and the opening 11 in the substrate 1, unevenness is created. To eliminate or reduce the unevenness, an auxiliary substrate (capillary force retaining complementary portion) 18 is provided to reduce a thickness of the application space 9 and retain a capillary force. The auxiliary substrate 18 eliminates the unevenness on the bottom side of the application space 9, and also adjusts the thickness (vertical thickness) of the application space 9 so that a blood sample can be satisfactorily sipped by capillarity in a position continuous with the opening 11. The auxiliary substrate 18 is made of a liquid impermeable material. Preferably, the auxiliary substrate 18 has the same thickness as the development flow channel and eliminates the unevenness from the development flow channel 2, but not limited to this. The auxiliary substrate 18 may have such a thickness as to merely reduce the unevenness from the development flow channel 2, and may be made of any material and may have any thickness. Further, the unevenness may still exist if as the application space 9 has a small thickness in this position and thus the capillary force can be retained. The auxiliary substrate 18 is not always separated from the substrate 1, but a thick portion corresponding to the auxiliary substrate 18 may be integrally formed with the substrate 1. The thick portion corresponding to the auxiliary substrate 18 is integrally formed, with the substrate 1, or a separate auxiliary substrate 18 is joined to the substrate 1 with high accuracy. Thus, when the space-forming member 8 is mounted on the substrate 1 to form the application space 9, the space-forming member 8 can be mounted on the substrate 1 without a warp, advantageously improving assembly accuracy.

Further, both side surfaces (specifically, both side surfaces of the substrate 1, the development flow channel 2, and the liquid impermeable sheet 7) in the chromatography development direction of the biosensor 20 are sealed by sealing portions 17. Thus, the blood sample applied to the application space 9 does not evaporate in the region from the application space 9 to the opened portion 10 in the development flow channel 2 because air cannot be released. The blood sample satisfactorily develops toward the opened portion 10 while development is facilitated. The sealing portions 17 may be formed by filling or joining sealers to the both sides, but not limited to this. For example, a laser light or the like may be applied to perform thermal fusion so as to prevent crush of a hole and passage of the liquid sample or the like. In FIGS. 8 and 10A to 10C, the both sides of the biosensor 20 are sealed, but not limited to this. A laser light extending in a chromatography development direction may be applied a predetermined width inside the both sides of the biosensor 20 to form grooves by thermal fusion in the left and right, and the blood sample may be developed only between the thermal fused grooves.

Figure 11A:
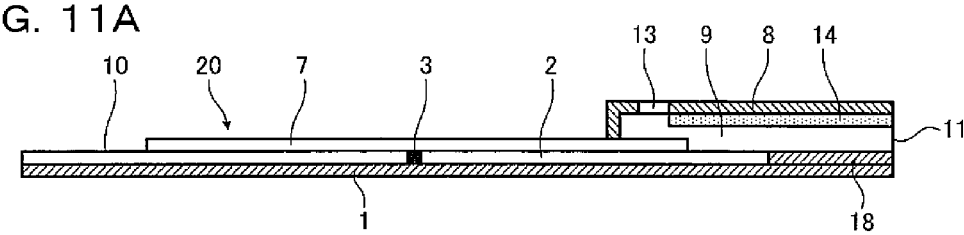
FIG. 11A is a sectional view of the biosensor.

Next, with reference to FIGS. 11A, 11B, 11C, 11D, 11E and 11F, a development state of the blood sample on the biosensor 20 will be described. FIG. 11A is a sectional view of the biosensor according to the embodiment of the present invention, and FIGS. 11B to 11F are sectional views showing development states of the blood sample in the biosensor according to the embodiment of the present invention when the blood sample is applied to the biosensor.

Figure 11B:
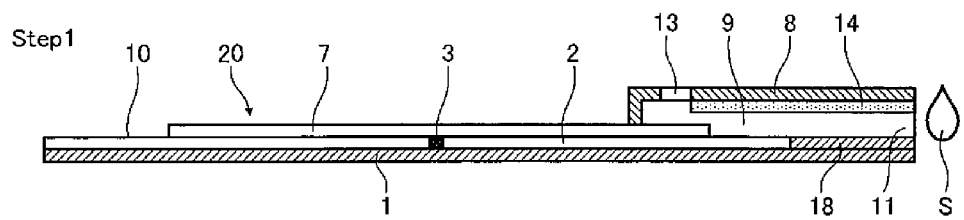
FIG. 11B is a sectional view showing an image of a development state when a blood sample is applied to the biosensor.
Figure 11C:
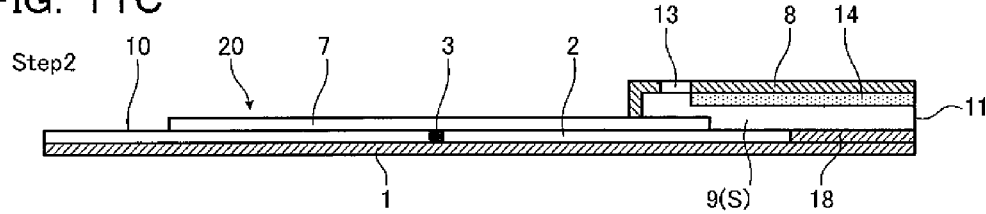
FIG. 11C is a sectional view showing an image of the development state when the blood sample is applied to the biosensor.
Figure 11D:
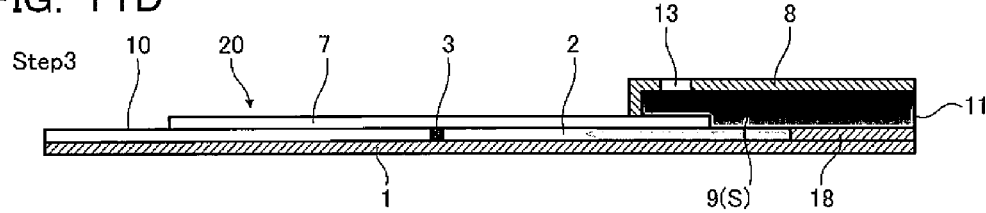
FIG. 11D is a sectional view showing an image of the development state when the blood sample is applied to the biosensor.

As shown in FIG. 11B, when a blood sample S is dropped (applied) to the opening 11 in the application space 9 (Step 1), a certain amount of blood sample S is sipped through the opening 11 into the application space 9 by capillarity, and the application space 9 is filled with the blood sample S (FIG. 11C: Step 2). When the blood sample S is sipped into the application space 9, a reagent (a labeling-reagent and a blood cell component shrinkage agent) of the reaction reagent 14 comes into contact with the blood sample S, and starts to be quickly dissolved. When the application space 9 is filled with the blood sample S, the dissolved reaction reagent reacts with the blood sample S and is diffused in the entire application space 9, and the blood sample S is developed in the development flow channel 2 (FIG. 11D: Step 3).

Figure 11E:
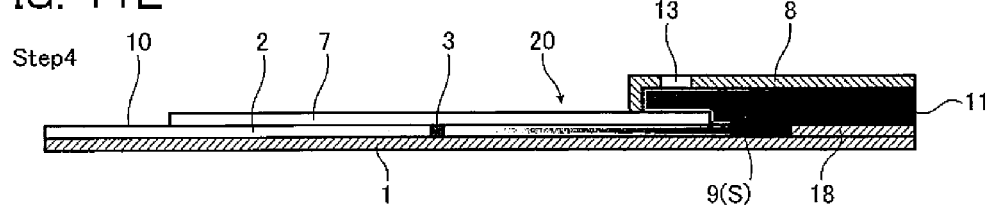
FIG. 11E is a sectional view showing an image of the development state when the blood sample is applied to the biosensor.
Figure 11F:
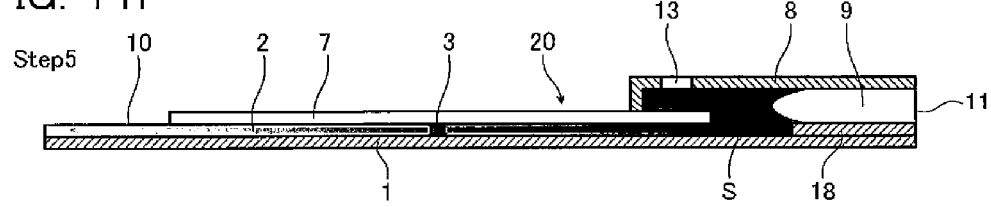
FIG. 11F is a sectional view showing an image of the development state when the blood sample is applied to the biosensor.

The blood sample S developed in the development flow channel 2 is developed while reacting with the reaction reagent, and reaches and then passes through the reagent-immobilized portion 3 (FIG. 11E: Step 4). When the blood sample S reaches the reagent-immobilized portion 3, and there is an analyte in the blood sample S, a specific reaction is performed between the reaction reagent, the analyte, and an immobilized-reagent. A color reaction caused by the reaction reagent occurs in the reagent-immobilized portion 3. The blood sample S further developed in the development flow channel 2 is prevented from water evaporation from a surface by the action of the liquid impermeable sheet 7 in a region of the development flow channel 2 covered with the liquid impermeable sheet 7, and water evaporation starts after the liquid specimen reaches the opened portion 10 that is not covered with the liquid impermeable sheet 7. This dry process helps development of the blood sample, and facilitates development of the blood sample S from the application space 9 to the opened portion 10. The application space 9 is a small space made of a liquid impermeable material, and the blood sample S is not retained in the small space but developed in the chromatography downstream direction by the development and the movement of the blood (FIG. 11F: Step 5). The reaction of the reaction reagent having appeared in the reagent-immobilized portion 3 through the steps can be visually checked or detected using a measurement device. This allows checking the presence and absence or the concentration of the analyte in the blood sample S.

The development flow channel 2 shown herein is a passage made of any material such that blood can be developed by a capillary force (force caused by capillarity), and in which the blood sample S can be developed. The development flow channel 2 may be made of any porous material such as filter paper, nonwoven fabric, membrane, fabric, and glass fiber as long as the material is wet with the blood sample S and can form a passage for development of the blood sample S. The passage may be formed of a hollow capillary, and such a hollow capillary may be made of a resin material or the like.

The reaction reagent mainly contains a labeling-reagent in addition to the blood cell component shrinkage agent. The labeling-reagent is obtained by labeling an antibody with a marker such as a gold colloid and is used as a detector of binding in the reagent-immobilized portion 3. The gold colloid is merely exemplary and any marker may be selected when necessary. For example, metal or nonmetal colloid particles, enzymes, proteins, coloring matters, fluorescent dyes, and dye particles such as latex may be used.

Further, any antibodies may be used for the reagent-immobilized portion 3 as long as a complex of the labeling-reagent and the analyte can be formed. Thus epitopes and affinities for the analyte may be the same or different from each other. Alternatively, the two antibodies may have different affinities but have the same epitope.

In the configuration of the biosensor shown in FIGS. 10A to 10C, the reagent-immobilized portion 3 is provided only at one point. The reagent-immobilized portion does not always have to be provided at one point. At least one point can be freely selected depending on the purpose (FIG. 8 shows a case where two reagent-immobilized portions 3 and 3' are provided). Further, the shape of the reagent-immobilized portion 3 on the development flow channel 2 does not always have to be linear and the reagent-immobilized portion may be freely shaped like a spot, a character, or a key. When the plurality of reagent-immobilized portions 3 and 3' are set, various positional relationships may be set such that the reagent-immobilized portions are spatially separated from each other or are in contact with each other like a single line.

A liquid impermeable sheet material 7 that covers the development flow channel 2 is composed of, for example, transparent PET tape. The liquid impermeable sheet material 7 tightly covers the development flow channel 2 other than a portion connecting to the application space 9 serving as the specimen application portion and a downstream end for receiving the liquid specimen.

The development flow channel 2 is covered with the liquid impermeable sheet material 7 and the sealing portion 17 seals the both sides of the development flow channel thus, so that a portion outside the application space 9 can be protected from dropping and contamination from the outside. Further, it is possible to prevent the developing blood sample from evaporating during the development of the blood sample, surely pass the blood sample through the reagent-immobilized portions 3 that serves as a reaction portion on the development flow channel 2, and allow the reagent-immobilized portions 3 to efficiently react with the analyte in the blood sample. In this case, the contamination from the outside refers to that the blood sample accidentally comes into contact with the reaction portions on the development flow channel 2 or an examinee directly touches the development flow channel 2 by hand or the like. The liquid impermeable sheet material 7 covering the development flow channel 2 covers the reagent-immobilized portion 3. The immobilizing portion 3 is a signal measuring portion of an analyte. Thus, the liquid impermeable sheet material 7 is preferably made of transparent materials and is thus at least in a transmissive state.

The substrate 1 is composed of a liquid impermeable sheet material such as a PET film, and may be transparent, translucent, or opaque. For example, when an optical detector is used as a measurement device, a transparent material is preferably used for measuring a transmitted light, and an opaque material is preferably used for measuring a reflected light. The substrate 1 may be made of synthetic resin materials such as ABS, polystyrene, or polyvinyl chloride, and liquid impermeable materials such as a metal or a glass.

The space-forming member 8 that forms the application space 9 sips and retains a certain amount of blood sample. The space-forming member 8 also provides protection against contamination by the blood sample to the outside when the biosensor is handled after the liquid specimen is applied. The space-forming member 8 may be synthetic resin materials such as ABS, polystyrene, or polyvinyl chloride, and liquid impermeable materials such as a metal or a glass. The space-forming member 8 is preferably transparent or translucent but may be colored. Further, any opaque material may be used.

Figure 12A:
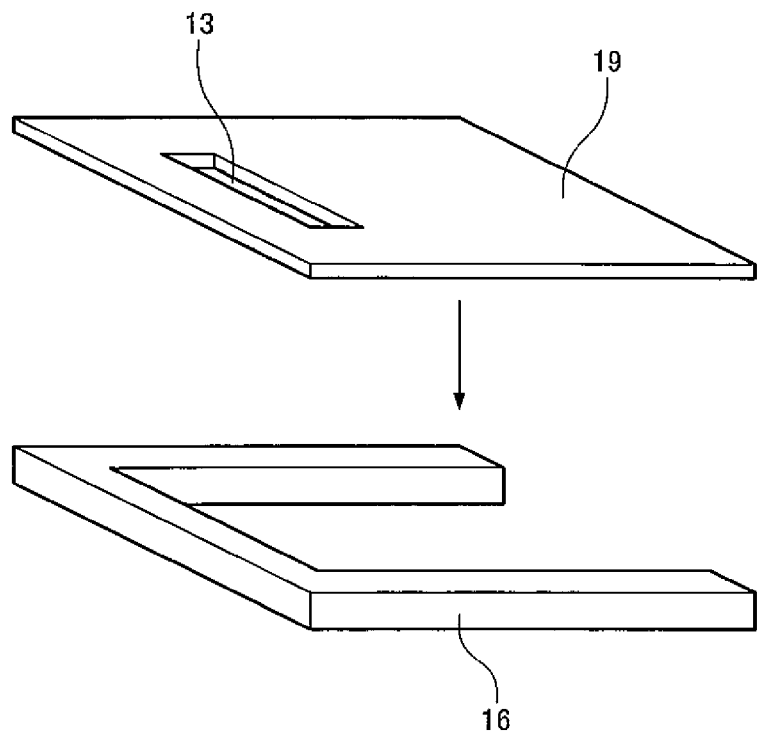
FIG. 12A is an exploded perspective view of a space-forming member that forms a specimen application portion of the biosensor.
Figure 12B:
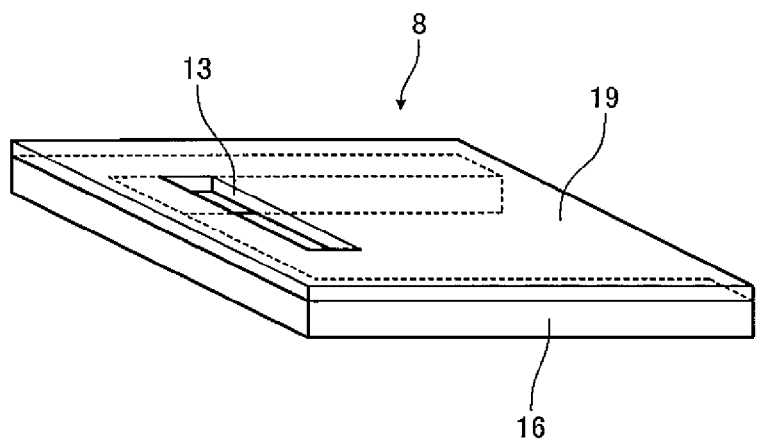
FIG. 12B is a perspective view of the space-forming member that forms the specimen application portion of the biosensor.

FIGS. 12A and 12B show a configuration of the space-forming member 8 of the application space 9 according to this embodiment, FIG. 12A is an exploded perspective view of the space-forming member 8, and FIG. 12B is a perspective view of the space-forming member 8. As shown in FIGS. 12A and 12B, the space-forming member 8 of the application space 9 placed on the downstream portion in the chromatography development direction of the substrate 1 may include, for example, a sheet material 19 that covers an upper surface of the application space 9, and a spacer 16 that covers both side surfaces and one end surface (downstream side surface in the chromatography development direction) of the application space 9 and defines a thickness of the application space as a small space. In this case, the sheet material 19 and the spacer 16 are bonded by any method. The sheet material 19 has an air hole 13, and the air hole 13 boosts a capillary flow for sipping the blood sample. Further, the volume of the blood sample that can be retained in the application space 9 can be satisfactorily defined by adjusting vertical and lateral sizes of the application space 9 and also a thickness of the spacer 16. The sheet material 19 may be subjected to any processing for boosting the capillary force.

The opened portion 10 at the chromatography downstream end in the development flow channel 2 is opened without being covered with the liquid impermeable sheet 7, so that the blood sample volatilizes or evaporates when or after reaching the opened portion 10. Further, the blood sample exudes to the opened portion 10 and the blood sample only on the opened portion 10 of the development flow channel 2 reaches the same level or substantially the same level as the liquid specimen on the development flow channel 2 in the application space 9. This facilitates evaporation and drying of the blood sample having reached the opened portion 10 in the development flow channel 2, and facilitates chromatography development from the upstream side to the downstream side without providing a water absorbing portion in the development flow channel 2.

With the above-described configuration, the reaction reagent is carried in the application space 9 that can sip and retain the blood sample by the capillary force. The development flow channel 2 is provided so that the upstream end enters the application space 9 only to the position on the deeper side in the suction direction than the opening 11 for sipping the blood sample in the application space 9. Thus, when the blood sample is applied and sipped into the application space 9, the reaction reagent is satisfactorily dissolved into the blood sample, and then the blood sample flows into the upstream end of the development flow channel 2 and is developed. This allows the blood sample into which the reaction reagent is uniformly dissolved to satisfactorily flow into the development flow channel 2, thereby allowing qualification or quantification with high accuracy and allowing measurement with high sensitivity.

Figure 18A:
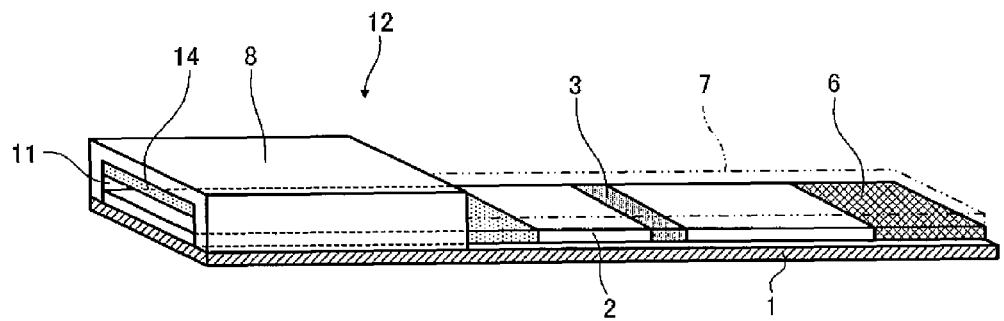
FIG. 18A is a perspective view of a biosensor of another comparative example.
Figure 18B:
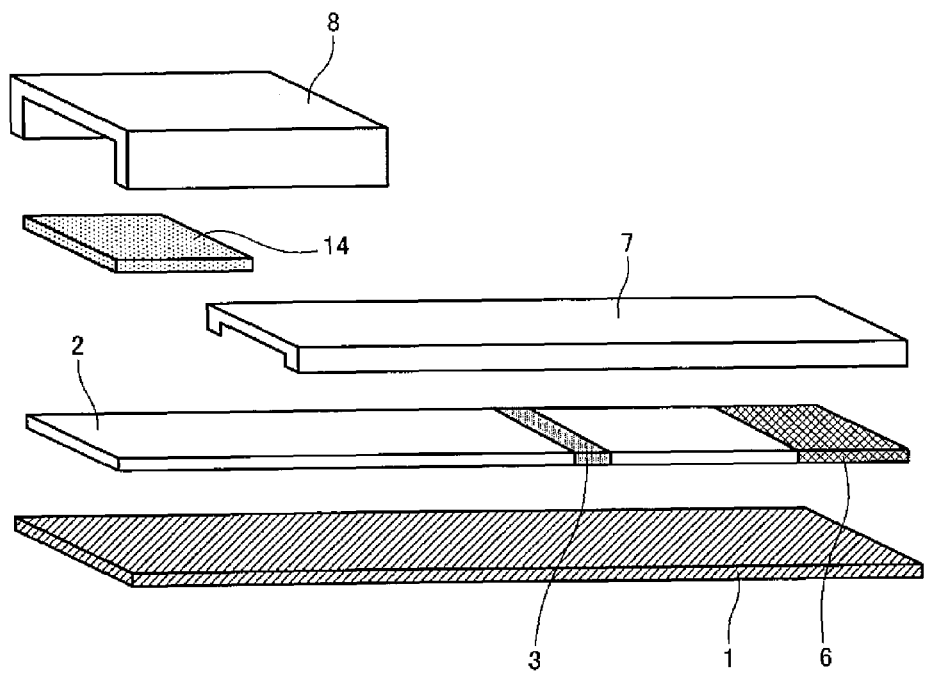
FIG. 18B is an exploded perspective view of the biosensor of another comparative example.
Figure 18C:
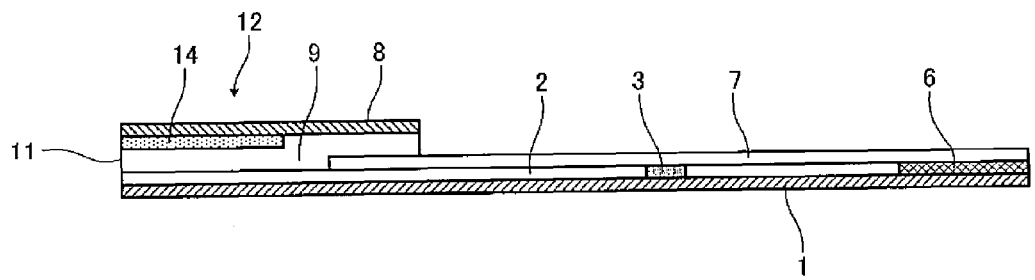
FIG. 18C is a sectional view when the biosensor of another comparative example is cut in a longitudinal direction.

FIGS. 18A to 18C show a comparative example. As a biosensor of the comparative example, when a development flow channel 2 has the same length as a substrate 1, an upstream end of the development flow channel 2 enters the entire region in a passage length direction of a capillary chamber 12, a reaction reagent 14 and also the upstream end of the development flow channel 2 are provided in and around an opening 11 as an inlet of the capillary chamber 12. Thus, a part of a liquid specimen applied to the capillary chamber 12 flows into the development flow channel 2 directly in a state where a labeling-reagent is not dissolved. Thus, the liquid specimen into which the labeling-reagent is nonuniformly dissolved flows in the development flow channel 2, which may prevent sufficient accuracy from being obtained in qualification measurement. On the other hand, the biosensor of this embodiment does not cause such defects as described above.

The auxiliary substrate 18 is provided on the bottom surface of the application space 9. The auxiliary substrate 18 is placed to reduce the unevenness corresponding to the thickness of the development flow channel 2 formed between the upstream end of the development flow channel 2 entering the application space 9 and the substrate 1, and thus reduce the thickness of the application space 9 and retain a capillary force. Thus, the capillary force for sipping the blood sample always satisfactorily and reliably acts in the application space 9, thereby increasing accuracy in qualification or quantification.

The reaction reagent is carried in the position not on the extension of the development flow channel 2 in the application space 9 along a thickness direction of the development flow channel 2. Thus, the reaction reagent is introduced into the development flow channel 2 in a state where the reaction reagent is uniformly dissolved into the blood sample applied to the application space 9, thereby obtaining measurement results with precision, high accuracy, and high sensitivity.

With the above-described configuration, the reaction reagent 14 contains the blood cell component shrinkage agent. Thus, when the blood cell component in the blood sample comes into contact with the blood cell component shrinkage agent as the reaction reagent, the blood cell component is quickly shrunk and the size thereof is made uniform. Thus, a nonuniform development state of the blood sample due to blood cell components having various sizes can be made uniform. This can also make the degree of reaction uniform, improve measurement variations, and achieve measurement with higher accuracy.

The space-forming member 8 that covers one end of the substrate 1 in the application space 9 includes the sheet material 19 facing the substrate 1 and the spacer 16 that defines the thickness of the application space 9. Thus, the volume of the blood sample that can be retained in the application space 9 can be obtained simply by changing the thickness of the spacer 16. This can further simplify the structure of the biosensor 20, and minimize variations in the degree of reaction due to variations in the structure of the biosensor 20, thereby achieving measurement with higher accuracy.

With the above-described configuration, the application space 9 is provided that can sip and retain the blood sample by a capillary force. Thus, a certain amount of blood sample can be reliably sipped. Also, at least a position facing the application space 9 in the application space 9 is made of a liquid impermeable material, and thus the application space 9 does not retain the blood sample, thereby achieving the application space 9 that can retain a blood sample of 10 μm or less.

Specifically, the present invention can minimize an undeveloped specimen, that is, a loss of specimen (dead volume) caused by water in the applied liquid specimen being retained by a construction material as in the conventional case, thereby significantly reducing the amount of specimen (blood sample) as compared with the conventional chromatographic sensor.

The biosensor is provided that can satisfactorily retain a certain amount of blood as a liquid specimen without using a dispenser, a dropper, or a syringe, also completely dissolve a labeling-reagent or other reaction reagents, significantly reduce the amount of applied blood, and further allow the blood in which the labeling-reagent is uniformly dissolved to satisfactorily flow into the development flow channel. This can provide the biosensor as an immuno-chromatographic sensor with precision, high accuracy, and high sensitivity based on an immune reaction that can increase measurement accuracy, also keep convenience in the conventional immuno-chromatographic sensor, achieve measurements performed anywhere at any time by anybody, and allow measurement with a small amount of liquid specimen such as blood.

The reaction reagent 14 is retained in the application space 9. Thus, the reaction reagent 14 can be completely dissolved without remaining in or being adsorbed by the application space 9. Thus, the degree of dissolution of the reaction reagent 14 becomes always constant. Also, the reaction reagent 14 comes into contact with the blood sample and is dissolved or hydrated in the blood sample in the application space 9, spreads over and reacts with the entire blood sample, and then can be developed in the development flow channel 2, thereby preventing remaining of the reaction reagent 14 and development of the blood sample that has not reacted with the reaction reagent.

The reaction reagent 14 can be 100% dissolved, and development of the unreacted blood sample can be prevented, thereby allowing measurement with higher precision and higher sensitivity.

Next, an analyzing device 104 will be simply described with reference to FIGS. 9 and 13. As shown in FIG. 9, to the analyzing device 104, the biosensor 20 can be mounted in a state where a part (the opening 11 in the application space 9 although not shown) of the biosensor 20 is exposed to the outside. When a blood sample S such as blood from a fingertip is applied in a state where the biosensor 20 is mounted to the analyzing device 104, the blood sample is sipped into the application space 9 by a capillary flow.

Figure 13:
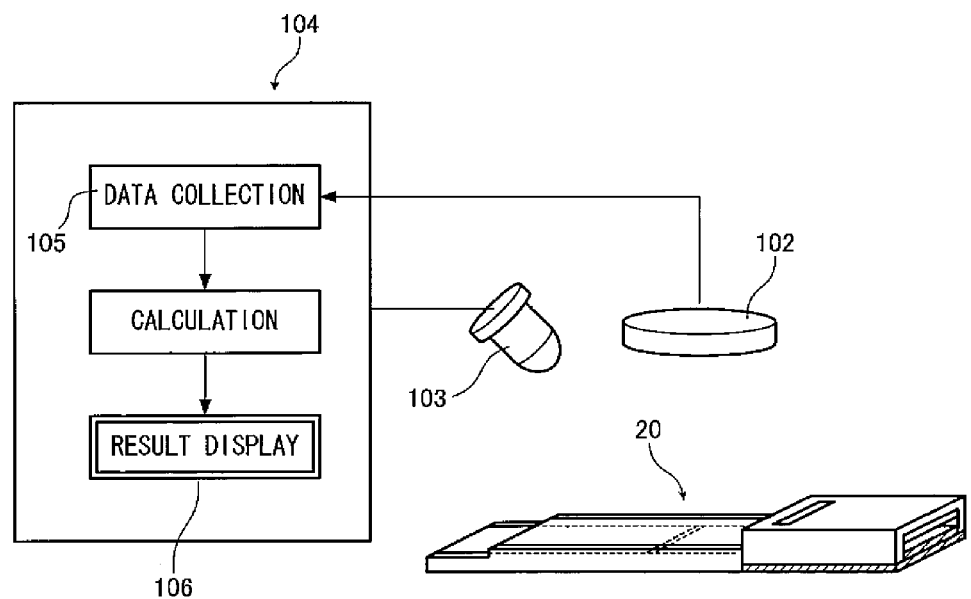
FIG. 13 simply shows a state of an analysis using an analyzing device that measures the biosensor.

As shown in FIG. 13, the analyzing device 104 includes an image sensor 102 and an application light emitting unit (such as an LED) 103 for measuring the state of the development flow channel 2 in the biosensor 20 and the degree of reaction of the reagent-immobilized portion 3, and a display portion 106. Any information captured by the image sensor 102 is collected by a data collecting portion 105 provided in the analyzing device 104. By a calculation based on the information, the presence and absence or the concentration of an analyte in the blood sample is displayed as a measurement result on the display portion 106.

The analyzing method by the analyzing device 104 is merely exemplary, and any other units (for example, an image sensor and an irradiation light, a photodiode and an irradiation light) may be used.

As such, qualitative or quantitative measurement of an analyte may be performed simply by an operation of applying a blood sample to the biosensor 20 mounted to the analyzing device 104.

INDUSTRIAL APPLICABILITY

A biosensor of the present invention is useful as a biosensor of an analyzing device for POCT that can achieve easy and quick measurement with high sensitivity and high accuracy when detecting an analyte in a liquid specimen based on a reaction such as an antigen-antibody reaction and performing quantitative or semi-quantitative measurement.

The invention claimed is:

1. A biosensor determining whether an analyte is present or not in a liquid specimen, or measuring a concentration of the analyte in the liquid specimen, comprising:
- a substrate including a first end where the liquid specimen is applied and a second end opposite to the first end;
- a specimen application portion adjacent the first end of the substrate, allowing the liquid specimen to be applied therein, the specimen application portion including a space-forming member and an application space enclosed by the space-forming member, the space-forming member extending along the substrate and including a top wall and opposing side walls;
- a reaction reagent retained on a surface of the space-forming member that faces the application space in the specimen application portion;
- a development flow channel formed downstream of the specimen application portion, in which the liquid specimen having reacted with the reaction reagent is developed toward the second end of the substrate, the development flow channel being made of a material such that the liquid specimen and the reaction reagent in the specimen application portion is developed by a capillary force;
- a measurement region disposed in the development flow channel that measures whether the analyte is present or not in the liquid specimen, or measures the concentration of the analyte in the liquid specimen; and
- an auxiliary substrate disposed on the substrate that adjusts a thickness of the application space,
- wherein the application space extends along the substrate from a first opening defined at a first end of the specimen application portion to a second opening defined at a second end of the specimen application portion, the first opening is located adjacent the first end of the substrate,
- wherein the first opening is sized to allow the liquid specimen to be drawn into the biosensor by a capillary force, and
- wherein the space-forming member is made of a liquid impermeable material, the space-forming member cooperates with a liquid impermeable surface such that the application space between the first and second openings is enclosed entirely by liquid impermeable material, wherein the liquid impermeable material enclosing the application space helps avoid retention of the liquid specimen on an inner surface of the application space, thereby facilitating entry of the liquid specimen to the development flow channel.

2. The biosensor according to claim 1, wherein the reaction reagent is provided in a position not in a surface on a portion of the development flow channel that is located in the specimen application portion.

3. The biosensor according to claim 1, wherein the development flow channel is placed along a surface of a substrate as a support, and the space-forming member has an upper surface having a back side spaced apart from and facing the surface of the substrate, and the reaction reagent is retained on the back side of the upper surface in the space-forming member.

4. The biosensor according to claim 1, wherein an air hole that facilitates suction of the liquid specimen into the application space is formed in the space-forming member.

5. The biosensor according to claim 1, wherein the measurement region includes a reagent-immobilized portion in which a reagent is immobilized as an immobilized-reagent that can behave a specific reaction with an analyte or a reaction reagent.

6. The biosensor according to claim 1, wherein the reaction reagent contains a labeling-reagent that can specifically react with the analyte or the immobilized-reagent.

7. The biosensor according to claim 6, wherein the labeling-reagent is obtained by labeling a reagent that can specifically react with the analyte or the immobilized-reagent with an insoluble granular marker.

8. The biosensor according to claim 7, wherein the insoluble granular marker is selected from the group including a colored polymer bead, a metal, an alloy, and a polymer dye particle.

9. The biosensor according to claim 5, wherein the specific reaction is an antigen-antibody reaction.

10. The biosensor according to claim 1, wherein the reaction reagent is a reagent other than a labeling-reagent.

11. The biosensor according to claim 1, wherein the biosensor comprises a liquid impermeable sheet that covers a surface of the development flow channel.

12. The biosensor according to claim 11, wherein the liquid impermeable sheet covers a range from a part of or neighborhood of the application space in the specimen application portion to at least the reagent-immobilized portion.

13. The biosensor according to claim 11, wherein the liquid impermeable sheet does not cover the development flow channel in a downstream end of the development flow channel.

14. The biosensor according to claim 1, wherein both side surfaces along a development direction of the development flow channel are covered or sealed.

15. The biosensor according to claim 1, wherein the liquid specimen is a blood sample.

16. The biosensor according to claim 15, wherein the reaction reagent contains a cell component shrinkage agent or a mixed reagent containing a cell component shrinkage agent, the cell component shrinkage agent reacts with a blood cell component in the blood sample, and the blood sample is developed in the development flow channel in a state where the blood cell component has been or is being shrunk.

17. The biosensor according to claim 15, wherein blood from a fingertip can be drawn sipped into the application space in the specimen application portion by a capillary force.

18. The biosensor according to claim 1, wherein the reaction reagent and the immobilized-reagent in a dry state are retained and immobilized in the biosensor, and are dissolved or hydrated into the liquid specimen.

19. The biosensor according to claim 18, wherein the reaction reagent in a solution state is applied to an inner surface of the space-forming member and then dried, and the immobilized-reagent in a solution state is applied to the development flow channel and then dried.

20. The biosensor according to claim 1, wherein a suction capacity of the application space in the specimen application portion is 10 μl or less.

21. The biosensor according to claim 1, wherein the application space is configured to be enclosed by the space-forming member made of a liquid impermeable material,
- an upstream portion of the development flow channel enters the application space from one end of the application space, and an entering position in the upstream end of the development flow channel is located on a deeper side in a suction direction than an opening for sipping the liquid specimen formed on the other end side of the application space.

22. The biosensor according to claim 21, wherein the development flow channel is supported on the substrate, the application space is formed as a required suction space by one end of the substrate corresponding to the upstream end of the development flow channel and the space-forming member covering one end of the substrate, the development flow channel has a predetermined thickness, and in the application space, an auxiliary substrate is provided that is placed to eliminate or reduce unevenness corresponding to the thickness of the development flow channel formed between the upstream end of the development flow channel entering the application space and the substrate, thereby reducing the thickness of the application space and retaining a capillary force.

23. The biosensor according to claim 21, wherein the development flow channel is supported on the substrate, the application space is formed as a required suction space by an auxiliary substrate that is formed of one end of the substrate corresponding to the upstream end of the development flow channel and defines the thickness of the specimen application portion, and the space-forming member that faces the substrate and covers one end of the substrate.

* * * * *

UNITED STATES PATENT AND TRADEMARK OFFICE
CERTIFICATE OF CORRECTION

PATENT NO. : 8,303,910 B2
APPLICATION NO. : 12/990313
DATED : November 6, 2012
INVENTOR(S) : Takahashi et al.

It is certified that error appears in the above-identified patent and that said Letters Patent is hereby corrected as shown below:

Column 38, line 40 (claim 17): after "drawn" delete "sipped".

Signed and Sealed this
Nineteenth Day of March, 2013

Teresa Stanek Rea
*Acting Director of the United States Patent and Trademark Office*